US009849258B2

(12) United States Patent
Klasek et al.

(10) Patent No.: US 9,849,258 B2
(45) Date of Patent: Dec. 26, 2017

(54) RESPIRATORY BREATHING APPARATUS

(75) Inventors: Paul Jan Klasek, Bonnyrigg Heights (AU); Liam Holley, Marrickville (AU); Quangang Yang, Kellyville (AU); Steven Paul Farrugia, Lugarno (AU); Timothy Tsun-Fai Fu, Pyrmont (AU); Robert Henry Frater, Lindfield (AU)

(73) Assignee: ResMed Limited (AU)

( * ) Notice: Subject to any disclaimer, the term of this patent is extended or adjusted under 35 U.S.C. 154(b) by 655 days.

(21) Appl. No.: 14/009,819

(22) PCT Filed: Apr. 5, 2012

(86) PCT No.: PCT/AU2012/000355
§ 371 (c)(1),
(2), (4) Date: Oct. 4, 2013

(87) PCT Pub. No.: WO2012/135912
PCT Pub. Date: Oct. 11, 2012

(65) Prior Publication Data
US 2014/0020684 A1    Jan. 23, 2014

(30) Foreign Application Priority Data

Apr. 5, 2011  (AU) ................................ 2011901262

(51) Int. Cl.
*A61M 16/00* (2006.01)
*A61M 16/10* (2006.01)
(Continued)

(52) U.S. Cl.
CPC .... *A61M 16/0066* (2013.01); *A61M 16/0069* (2014.02); *A61M 16/109* (2014.02);
(Continued)

(58) Field of Classification Search
CPC .. A61M 2016/0027; A61M 2016/0039; A61M 16/0066; A61M 16/0069;
(Continued)

(56) References Cited

U.S. PATENT DOCUMENTS

| 4,164,690 A | * | 8/1979 | Muller ............... F04D 25/0653 |
| | | | 310/63 |
| 5,405,251 A | * | 4/1995 | Sipin ..................... A61M 1/101 |
| | | | 415/146 |

(Continued)

FOREIGN PATENT DOCUMENTS

| CN | 101583395 A | 11/2009 |
| GB | 2386842 A | 10/2003 |

(Continued)

OTHER PUBLICATIONS

Machine translation of JP 63285294 A.*

(Continued)

*Primary Examiner* — Tan-Uyen (Jackie) T Ho
*Assistant Examiner* — Joseph D Boecker
(74) *Attorney, Agent, or Firm* — Lerner, David, Littenberg, Krumholz & Mentlik, LLP

(57) ABSTRACT

A respiratory apparatus comprising a base and removable chamber, wherein the chamber is configured to hold a supply of water and include a blower arrangement adapted to provide a supply of pressurized air or gas to the supply of water. In certain embodiments the respiratory apparatus includes a split motor, wherein the stationary components are located within a base and the rotating portions are located within a chamber.

20 Claims, 24 Drawing Sheets

(51) Int. Cl.
*A61M 16/16* (2006.01)
*F04D 25/06* (2006.01)

(52) U.S. Cl.
CPC ........ *A61M 16/1075* (2013.01); *A61M 16/16* (2013.01); *A61M 16/161* (2014.02); *A61M 16/107* (2014.02); *A61M 16/1055* (2013.01); *A61M 2016/0027* (2013.01); *A61M 2016/0039* (2013.01); *A61M 2205/332* (2013.01); *A61M 2205/3317* (2013.01); *A61M 2205/3365* (2013.01); *A61M 2205/3368* (2013.01); *A61M 2205/3375* (2013.01); *A61M 2205/42* (2013.01); *F04D 25/0653* (2013.01)

(58) Field of Classification Search
CPC .............. A61M 16/1075; A61M 16/16; A61M 16/161; A61M 2205/3317; A61M 2205/3365; A61M 2205/3368; A61M 2205/3375; A61M 2205/42; F04D 25/02; F04D 25/06; F04D 29/04; F04D 13/0666; H02K 5/12; H02K 5/128
See application file for complete search history.

(56) References Cited

U.S. PATENT DOCUMENTS

| | | | | |
|---|---|---|---|---|
| 5,947,703 A * | 9/1999 | Nojiri | ................... | A61M 1/101 415/229 |
| 6,232,696 B1 * | 5/2001 | Kim | ................... | F04D 25/0653 310/156.37 |
| 6,302,105 B1 * | 10/2001 | Wickham | .......... | A61M 16/0057 128/200.27 |
| 6,637,433 B2 * | 10/2003 | Schob | ............... | A61M 16/0057 128/204.19 |
| 7,913,689 B2 | 3/2011 | Henry et al. | | |
| 8,092,460 B2 * | 1/2012 | Geist | ................. | A61B 17/7083 606/279 |
| 8,272,837 B2 | 9/2012 | Kenyon et al. | | |
| 8,453,640 B2 * | 6/2013 | Martin | .............. | A61M 16/0066 128/203.17 |
| 8,459,259 B2 | 6/2013 | Klasek et al. | | |
| 2002/0000228 A1 | 1/2002 | Schoeb | | |
| 2005/0287022 A1 * | 12/2005 | Yaegashi | ................ | A61M 1/101 417/420 |
| 2007/0152526 A1 * | 7/2007 | Tsai | ....................... | H02K 21/24 310/156.32 |
| 2007/0297923 A1 * | 12/2007 | Tada | ..................... | A61M 1/101 417/356 |
| 2009/0099572 A1 * | 4/2009 | Geist | .................. | A61B 17/7083 606/96 |
| 2009/0136341 A1 * | 5/2009 | Kenyon | ............ | A61M 16/0057 415/203 |
| 2009/0194106 A1 | 8/2009 | Smith et al. | | |
| 2010/0065051 A1 | 3/2010 | Potharaju et al. | | |
| 2010/0132708 A1 * | 6/2010 | Martin | ............. | A61M 16/0066 128/204.17 |
| 2011/0129373 A1 * | 6/2011 | Mori | ..................... | A61M 1/101 417/420 |

FOREIGN PATENT DOCUMENTS

| | | | |
|---|---|---|---|
| JP | 63285291 A | * | 11/1988 |
| JP | 63285294 A | * | 11/1988 |
| JP | 2002511786 A | | 4/2002 |
| JP | 2002227792 A | | 8/2002 |
| JP | 2004028032 A | | 1/2004 |
| JP | 2010508957 A | | 3/2010 |
| JP | 2011502019 A | | 1/2011 |
| WO | 9947197 A1 | | 9/1999 |
| WO | 2008056993 A2 | | 5/2008 |
| WO | 2009058032 A1 | | 5/2009 |
| WO | 2010031126 A1 | | 3/2010 |

OTHER PUBLICATIONS

Machine translation of JP 63285291 A.*
Extended European Search Report for Application No. EP12767494 dated Aug. 5, 2014.
International Search Report and Written Opinion for Application No. PCT/AU2012/000355 dated Jul. 5, 2012.

* cited by examiner

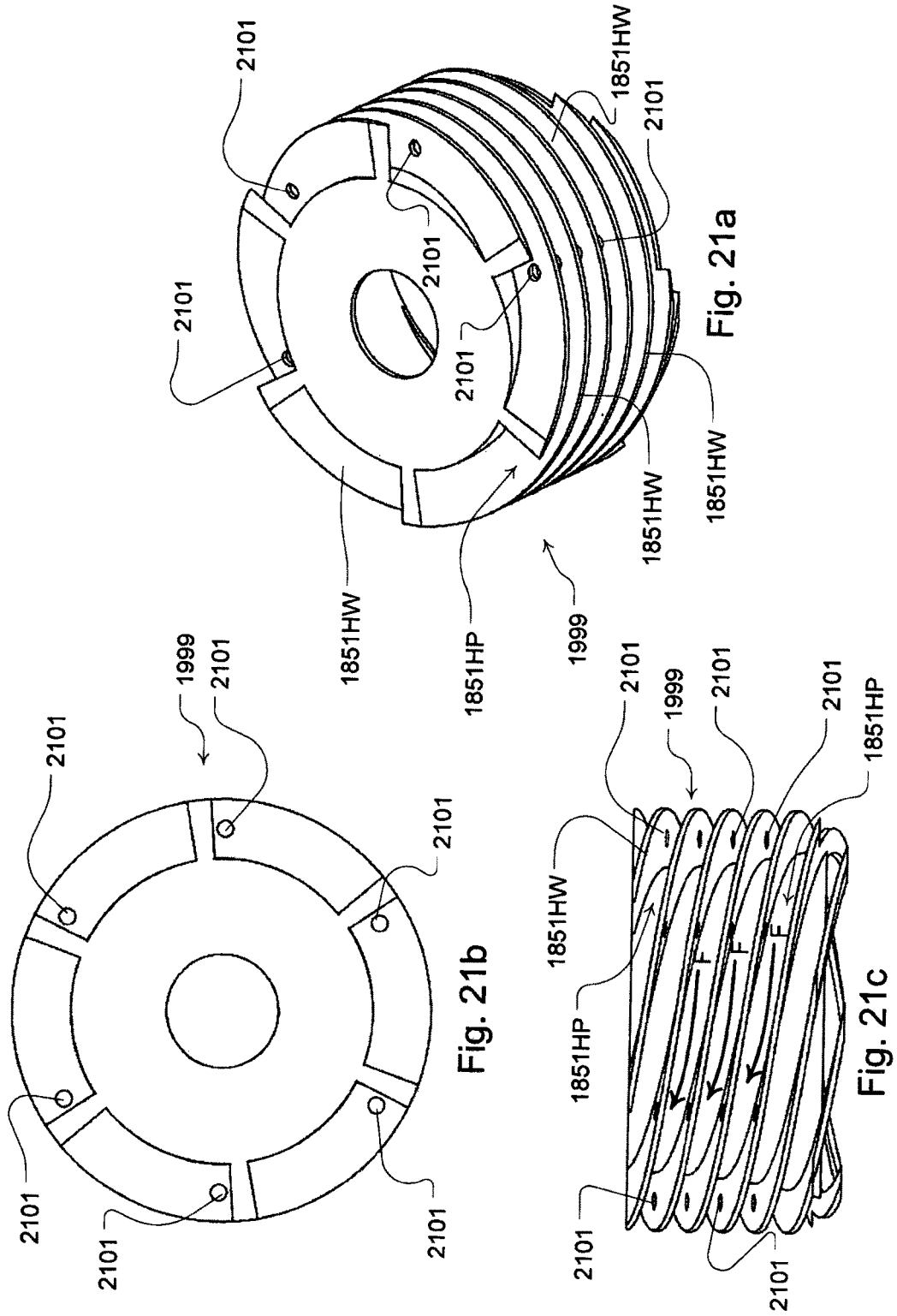

RESPIRATORY BREATHING APPARATUS

CROSS REFERENCE TO RELATED APPLICATIONS

The present application is a national phase entry under 35 U.S.C. §371 of International Application No. PCT/AU2012/000355 filed Apr. 5, 2012, published in English, which claims priority from Australia Provisional Patent Application No. 2011901262 filed Apr. 5, 2011, all of which are hereby incorporated herein by reference.

FIELD OF TECHNOLOGY

The present technology relates to a respiratory breathing apparatus used in all forms of respiratory ventilation systems including invasive and non-invasive ventilation, Continuous Positive Airway Pressure (CPAP), Bi-Level therapy and treatment for sleep disordered breathing (SDB) conditions such as Obstructive Sleep Apnea (OSA), and for various other respiratory disorders and diseases such as chronic obstructive pulmonary disease (COPD), chronic bronchitis, emphysema, chronic heart failure, muscular dystrophy or other such respiratory disorders.

BACKGROUND OF TECHNOLOGY

Respiratory treatment apparatuses involves the delivery of a pressurized breathable gas, such as air, oxygen enriched air or oxygen, to a patient's airways using a conduit and patient interface device. Gas pressures employed typically range from 4 cm $H_2O$ to 30 cm $H_2O$, at flow rates of up to 180 L/min (measured at the mask), depending on patient requirements. For CPAP the pressurized gas acts as a pneumatic splint for the patient's airway in a CPAP device, preventing airway collapse, especially during the inspiratory phase of respiration. For ventilation the apparatus is designed to move breathable gas into and out of the patients' lungs.

The advantages of incorporating humidification of the air supply to a patient are known, and respiratory apparatuses are known which incorporate humidifying devices. Such respiratory apparatuses commonly have the ability to alter the humidity of the breathable gas in order to reduce drying of the patient's airway and consequent patient discomfort and associated complications. The use of a humidifier unit placed between the flow generator and the patient mask produces humidified gas that minimizes drying of the nasal mucosa and increases patient airway comfort. In addition in cooler climates, warm air applied generally to the face area in and about the mask is more comfortable than cold air.

Many humidifier types are available, including humidifier that are either integrated with or configured to be coupled to the relevant respiratory apparatus. If integrated within the relevant respiratory apparatus the humidifier is generally formed in a separate portion of the apparatus to the blower to prevent water entering the blower. While passive humidifiers can provide some relief, generally a heated humidifier is required to provide sufficient humidity and temperature to the air so that the patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub.

Respiratory apparatuses typically include a blower integrated within the apparatus to provide a supply of respiratory gas. The blower comprises an integrated motor having a stationary component and rotating component (or rotor) that are adapted to drive an impeller. The rotating component includes a rotor or shaft coupled to a magnet and the stationary component includes a stator comprising a plurality of wound coils. The stator provides an electromagnetic drive to rotate the magnet and coupled rotor. The impeller is commonly coupled to the shaft or rotor such that it is induced to rotate with the rotor or shaft. The stationary component and rotating components are located together as a motor unit within the blower. Typically the motor has a cylindrical construction, such that the stator with wound coils is aligned vertically to surround the rotor and magnet. Thus, when the motor is energized the wound coils create a magnetic field that causes the magnet to rotate. As the magnet is coupled to the rotor and the rotor is coupled to the impeller, the rotor and impeller are also caused to rotate with the magnet.

U.S. Pat. No. 6,302,105 describes having an impeller located within a separate housing to the motor. However, the motor still comprises a stationary component (wound coils) and rotating component (rotor and magnet). The impeller is not directly coupled to the rotating portion of the motor but is driven to rotate by the addition of extra magnets on the impeller that induce the impeller to rotate in synchrony with the rotating portion of the motor. The separation of the impeller from the motor is said to provide a disposable air path.

Respiratory apparatuses have also been developed to reduce the dangers of biological contamination, such as when used in hospitals for multiple patients. A bacteriological filter may be included to prevent biological material being forced back into the apparatus. In other systems, the respiratory apparatus may be configured to be cleanable or autoclavable.

SUMMARY OF THE TECHNOLOGY

One aspect of the disclosed technology relates to a respiratory apparatus having an integrated blower and humidifier.

Another aspect of the disclosed technology relates to a respiratory apparatus including a blower having an impeller that is driven by a motor, wherein the rotating component of the motor is disengaged or separated from the stator component of the motor.

Another aspect of the disclosed technology relates to a respiratory apparatus comprising a chamber including an air inlet and an air outlet; a base configured to receive the chamber thereon; and a motor configured to provide a supply of pressurized air to the air outlet, the motor having a stationary portion and a rotating portion, wherein the stationary portion of the motor is located in the base and the rotating portion of the motor is located in the chamber. The rotating portion of respiratory apparatus may comprise at least one impeller that is electromagnetically driven to rotate by the stationary portion in the base.

Another aspect of the disclosed technology relates to a respiratory apparatus comprising a blower having an impeller configured to provide a supply of pressurized air or gas, a humidifier configured to humidify the supply of pressurized air or gas, wherein the blower and the humidifier are arranged within a chamber, the chamber being configured to be coupled to a base, and the base comprises the electronic and control components adapted to drive the blower.

In another aspect of the technology the respiratory apparatus includes a chamber configured to provide a humidified and pressurized supply of air or gas, the chamber structured to be removably coupled to a base, wherein the base controls the operation of the components within the chamber. In certain forms the chamber may be disposable.

In some embodiments, the rotating portion may include at least one impeller that is magnetically driven to rotate by the stationary portion in the base. Optionally, a magnet may be coupled to the impeller. In some cases, the impeller may be constructed of a magnetized material, for example a magnetized polymer. Still further, the rotating portion may form part of a blower within the chamber. The blower may include an inlet flow path configured to direct the air from the air inlet to the impeller. The blower may include a volute configured to direct the pressurized air from the impeller towards one or more blower outlets. Optionally, the stationary portion may include a stator having a plurality of wound coils.

In some embodiments, the chamber may be configured to hold a supply of water to humidify the supply of pressurized air or gas prior to exiting through the air outlet. The supply of water may be heated by a heater element. The heater element may be located in the base and/or the heater element may be located in the chamber.

In some embodiments, for operation, the stationary portion and the rotating portion may be arranged in a stacked configuration separated by a housing wall of the base. In some embodiments, for operation, the stationary portion and the rotating portion may be arranged in a radial configuration separated by a housing wall of the base. Optionally, the rotating portion and the stationary portion may be further separated by a wall of the chamber. Also, the chamber may have a container configuration including a bottom wall and side wall. Optionally, the chamber may include a spiral flow pathway. In some versions, a blower partition is configured to expel pressurized air into the spiral flow pathway at a bottom wall of the chamber and the spiral flow pathway is configured to deliver the pressurized air to the air outlet proximate the top of the chamber.

Some embodiments of the present technology may include a respiratory apparatus for generation of a pressurized flow of treatment air for a patient interface. The apparatus may include a blower partition with an included magnetic impeller to generate the pressurized flow of treatment air. The blower partition may have an upstream flow path and a downstream flow path relative to the impeller. The apparatus may also include a humidifier chamber configured to hold a fluid for humidification of the flow of treatment air. The apparatus may also include a base housing. The base housing may include field coils to influence movement of the impeller. The base housing may be configured to couple with the humidifier chamber. In some versions, the blower partition may be integrated or insertable within the humidifier chamber for operation. In some versions, the blower partition does not include field coils. Optionally, during operation, humidification water may reside within a volume of the humidifier chamber to surround an impeller portion of the blower partition. Still further, the magnetic impeller and the field coils may be arranged in a stacked configuration separated by a wall of the base housing. Similarly, the magnetic impeller and the field coils may be arranged in a radial configuration separated by the base housing. The magnetic impeller and the field coils may be further separated by a wall of the humidifier chamber. The humidifier chamber may have a container configuration including a bottom wall and side wall. It may also include a spiral flow pathway. In some cases, the downstream flow path may be configured to expel pressurized air into the spiral flow pathway proximate to a bottom wall of the humidifier chamber and the spiral flow pathway may be configured to deliver the pressurized air to an air outlet proximate to a top of the humidifier chamber. Optionally, the base housing may further include a user interface for controlling operation of the impeller. In some versions, the apparatus may also include a sensor to detect a vibration of the impeller that may be indicative of impeller wear. In some such embodiments, an inlet pathway, such as the upstream flow path, may include a muffler. Similarly, an outlet pathway, such as the downstream flow path, of the apparatus may include a muffler. Optionally, each field coil may include a vibration absorber.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 16b is a top plan view illustration of components of the embodiment FIG. 16a;

FIG. 18b is a plan view illustration of the chamber example of FIG. 18a;

FIGS. 21a to 21c are views (perspective, top plan and front view respectively) of an example spiral humidification flow insert in some embodiments;

DETAILED DESCRIPTION OF ILLUSTRATED EXAMPLES

The following description is provided in relation to several examples (most of which are illustrated, some of which may not be) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The subject headings used in the detailed description are included only for the ease of reference of the reader and should not be used to limit the subject matter found throughout the disclosure or the claims. The subject headings should not be used in construing the scope of the claims or the claim limitations.

Respiratory Apparatus

Figure 1A:
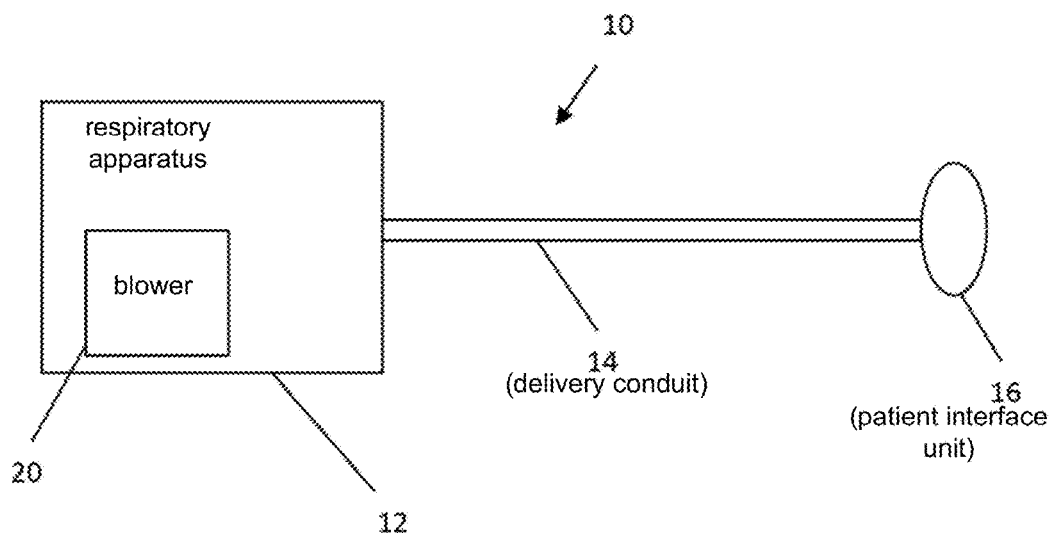
FIG. 1a is schematic of an example respiratory system.

As schematically shown in FIG. 1a a respiratory system 10 generally includes a respiratory apparatus 12, an air delivery conduit 14 (also referred to as an air delivery tube or tubing) and a patient interface unit 16. In use the respiratory apparatus 12 includes a blower or pressure generating device 20 for generating breathable gas at a positive pressure, the pressurized gas is delivered to the patient interface unit 16 via the air delivery conduit 14. The air delivery conduit 14 is coupled to an outlet of the blower or pressure generating device 20 at one end and to an inlet of the patient interface unit 16 at the opposite end. For non-invasive ventilation the patient interface 16 comfortably engages the patient's face and provides a seal. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face. For non-invasive forms of ventilation the patient interface unit 16 may include a tracheotomy tube.

Figure 1B:
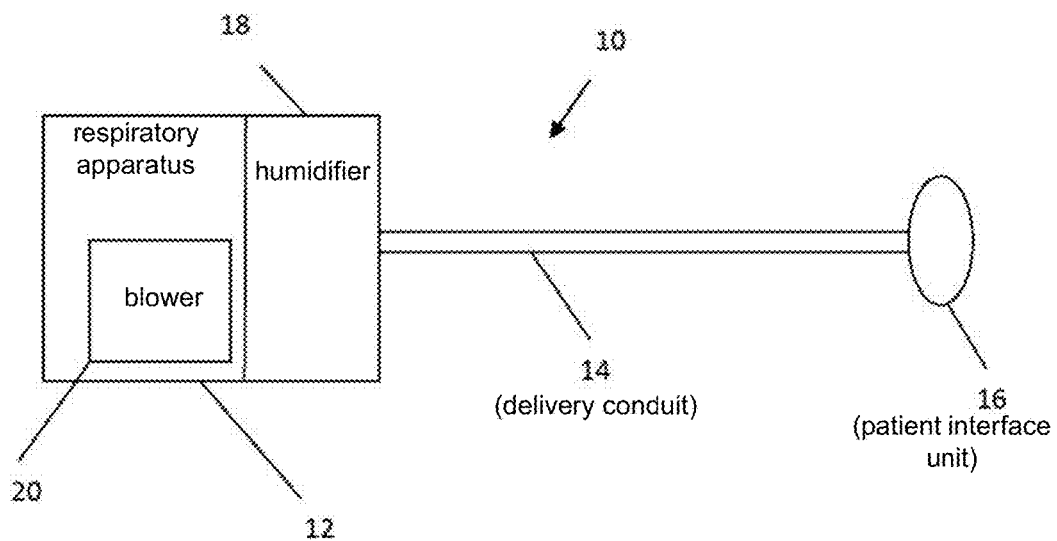
FIG. 1b is schematic of an example respiratory system including a humidifier.
Figure 2:
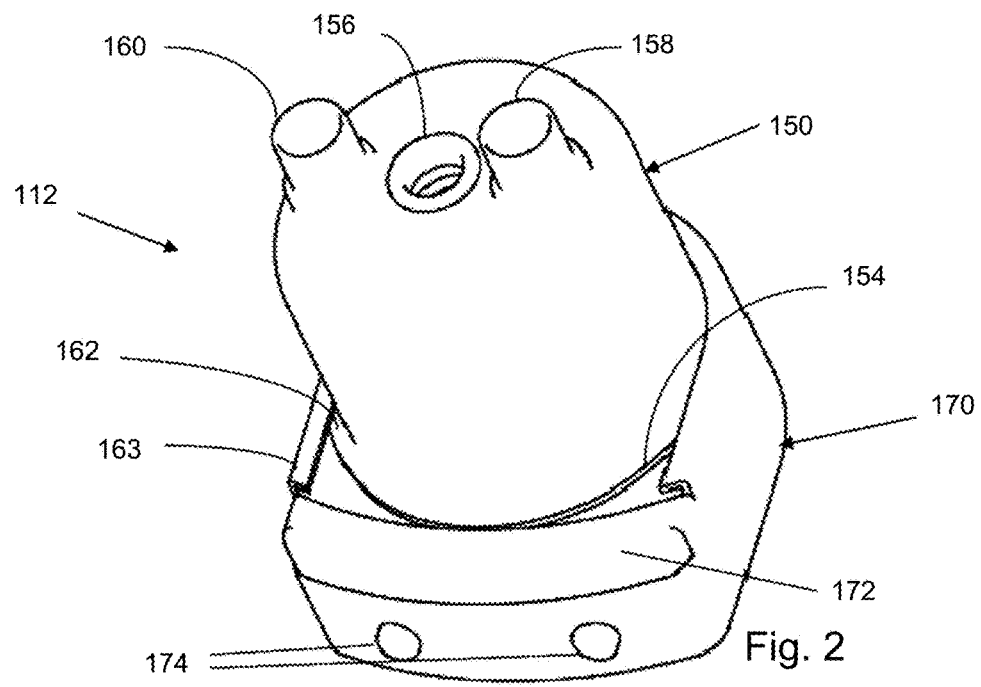
FIG. 2 is a perspective view of an example apparatus of the present technology.

In certain embodiments, a humidifier 18 may be incorporated or integrated into the respiratory apparatus 12 or otherwise provided downstream of the respiratory apparatus 12. In such embodiments, the air delivery conduit 14 may be provided between the patient interface unit 16 and the outlet of the humidifier 18 as schematically shown in FIG. 1b.

Generally, a heated humidifier is used to provide sufficient humidity and temperature to the air so that the patient will be comfortable. In certain embodiments, the air delivery conduit 14 may be heated to heat the gas and prevent "rain-out" or condensation forming on the inside of the conduit as the gas is supplied to the patient. In this arrangement, the air delivery conduit 14 may include one or more wires or sensors associated with heating.

FIGS. 2-11 illustrate certain embodiments of respiratory apparatuses of the technology. It is noted that like numbers are used to indicate similar components in the different embodiments. The respiratory apparatuses 112, 212, 312 include a chamber 150, 250, 350 and a base 170, 270, 370. The chamber 150, 250, 350 is configured to be removably coupled to the base 170, 270, 370. The chamber 150, 250, 350 encompasses a pressure generating device or blower 120, 220, 320 and may also form a water chamber to hold a supply of water 140 for humidification. Thus, humidification and pressure generating functions may be performed within a common chamber such as the chamber 150, 250, 350 reducing the overall size of the respiratory apparatus 112, 212, 312. However, it is noted that water 140 is not required to be added to the chamber 150, 250, 350 such that the device may only provide a supply of pressurized air or gas. However, in some embodiments, the common chamber may permit a volume of water or other liquid, such as for humidification, to surround a periphery that includes movable parts of the motor/blower of the pressure source, such as the impeller portion of a blower partition. Such a configuration may permit noise reduction or noise absorption benefits due to some motor vibration being absorbed by the proximal water rather than being propagated, in addition to facilitating an increase in the contact area between the water and the air flow from the blower to increase humidification efficiency. The proximity may also promote an absorption of heat from the motor components into the water to beneficially warm the water and cool the motor.

The blower of the respiratory apparatuses 112, 212, 312 in FIGS. 2-11 may include a split motor configuration. In such an arrangement the stationary components 130s of the motor 130 are located in the base 170, 270, 370 of the apparatus and the rotating components 130r of the motor 130 are located in the chamber 150, 250, 350 (see FIG. 12). The stationary components 130s electromagnetically drive the rotation of the rotating components 130r by the conduction of the magnetic flux through the base 170, 270, 370 to the chamber, 150, 250, 350. The split motor has a stacked or pancake arrangement in some embodiments such that the stator 178 with wound coils 179 is aligned horizontally in the base 170; 270, 370 and impeller 136 and magnet 196 are horizontally aligned in the chamber and positioned above the stator 178 in use. The base 170, 270, 370 does not comprise any rotating components. In such a configuration the electronic drive components of the motor are separate or outside the respiratory air path and the impeller and rotating components are within the respiratory air path. Thus, in some embodiments, a case or housing wall of the base and/or a wall of the chamber may separate, or form a barrier between, the rotor (e.g., impeller with magnets) and the stator (e.g., the control coils.)

The respiratory apparatus 112, 212, 312 may comprise sensors (not shown) such as pressure, flow, temperature and/or humidity sensors as are commonly used in such devices. Pressure and/or flow sensors may be used to control the operation of the apparatus.

A respiratory apparatus 112 according to a certain embodiment as illustrates in FIGS. 2-5 will be described in more detail below.

Base

The base 170 comprises a top cover 144, a PCB 176, a stator 178 including wound coils 179 (also known as motor stator component) and a base bottom 148. The stator 178 being part of a motor adapted to drive an impeller 136 of a blower 120 (as described in more detail below). The impeller 136 being located within a chamber 150. The base 170 may also include other electronics to control the apparatus and therapies provided by the apparatus. The base 170 may include one or more user interfaces 174 such as user buttons (see FIG. 2), dials, touch screen or display screen other user interface systems. The base may also be configured to communicate with or be coupled to a computer or other user interface system.

Figure 3:
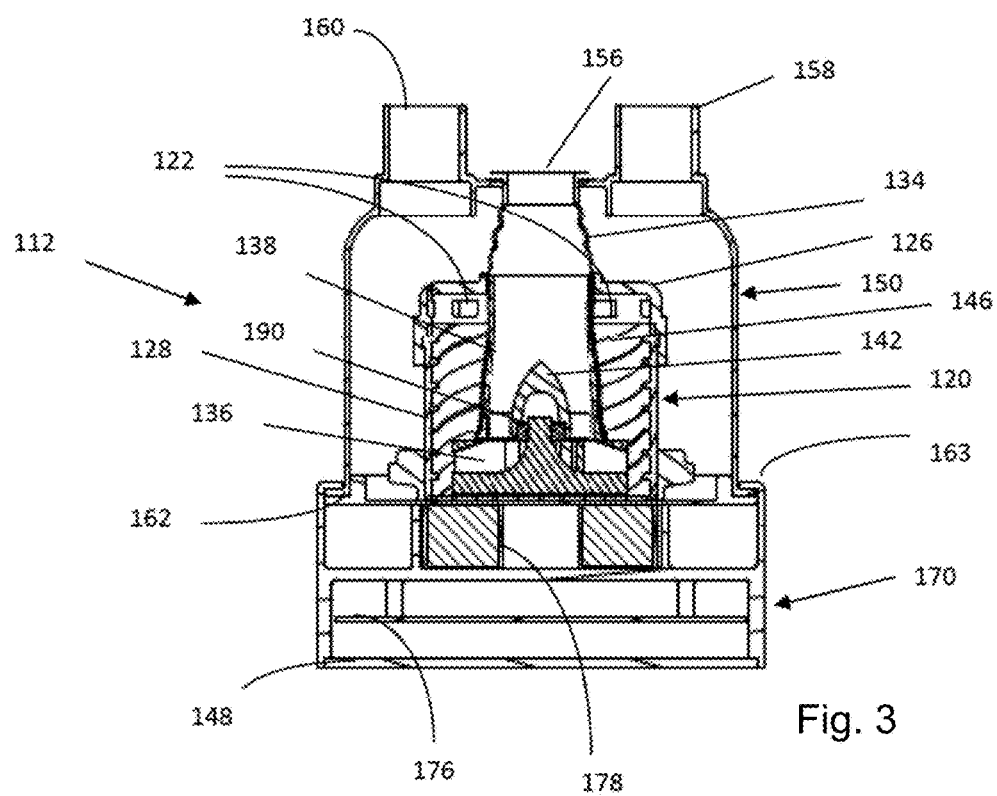
FIG. 3 is a cross-sectioned side view of the apparatus of FIG. 2.
Figure 4:
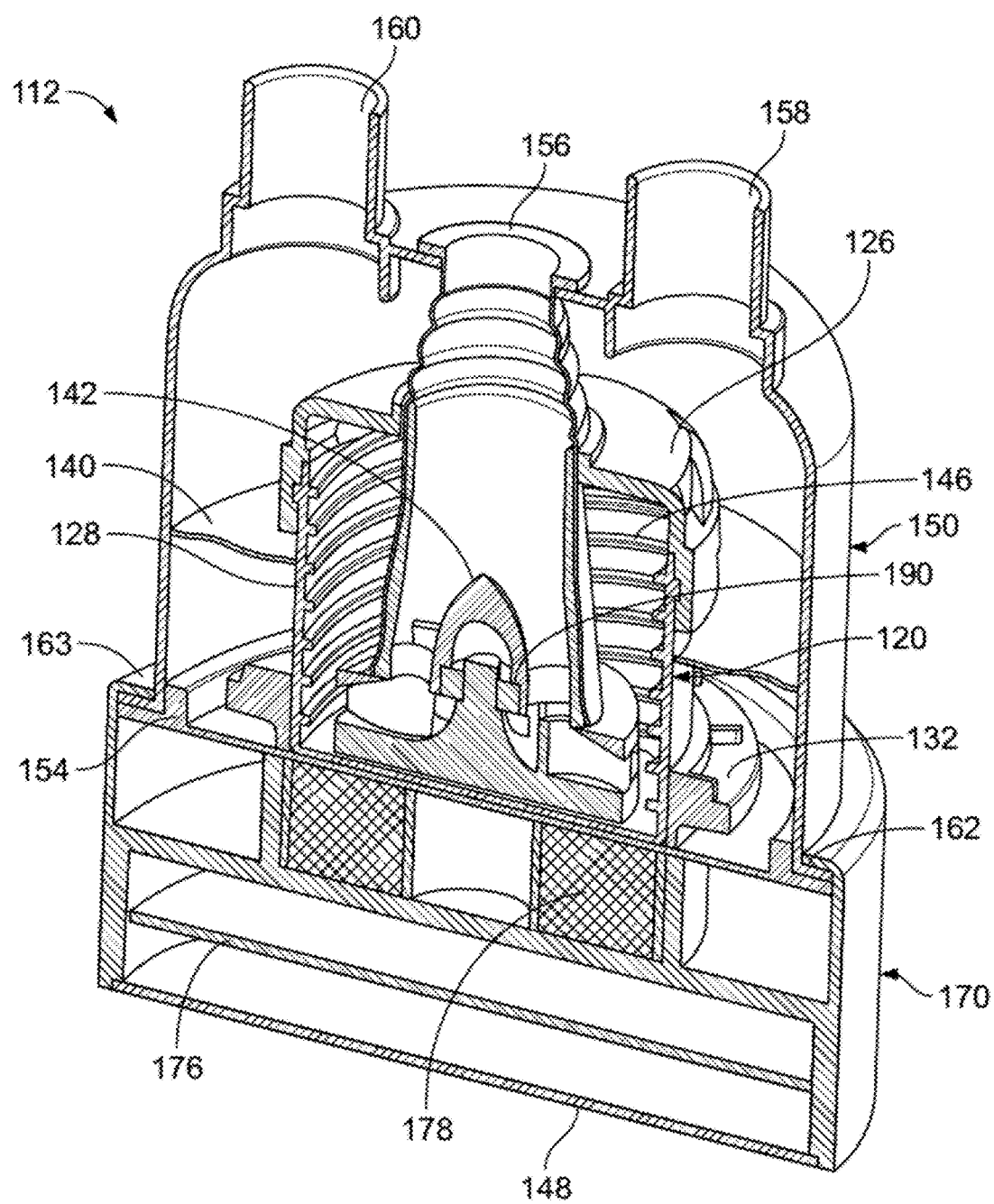
FIG. 4 is a cross-sectioned perspective view of the apparatus of FIG. 2.
Figure 5:
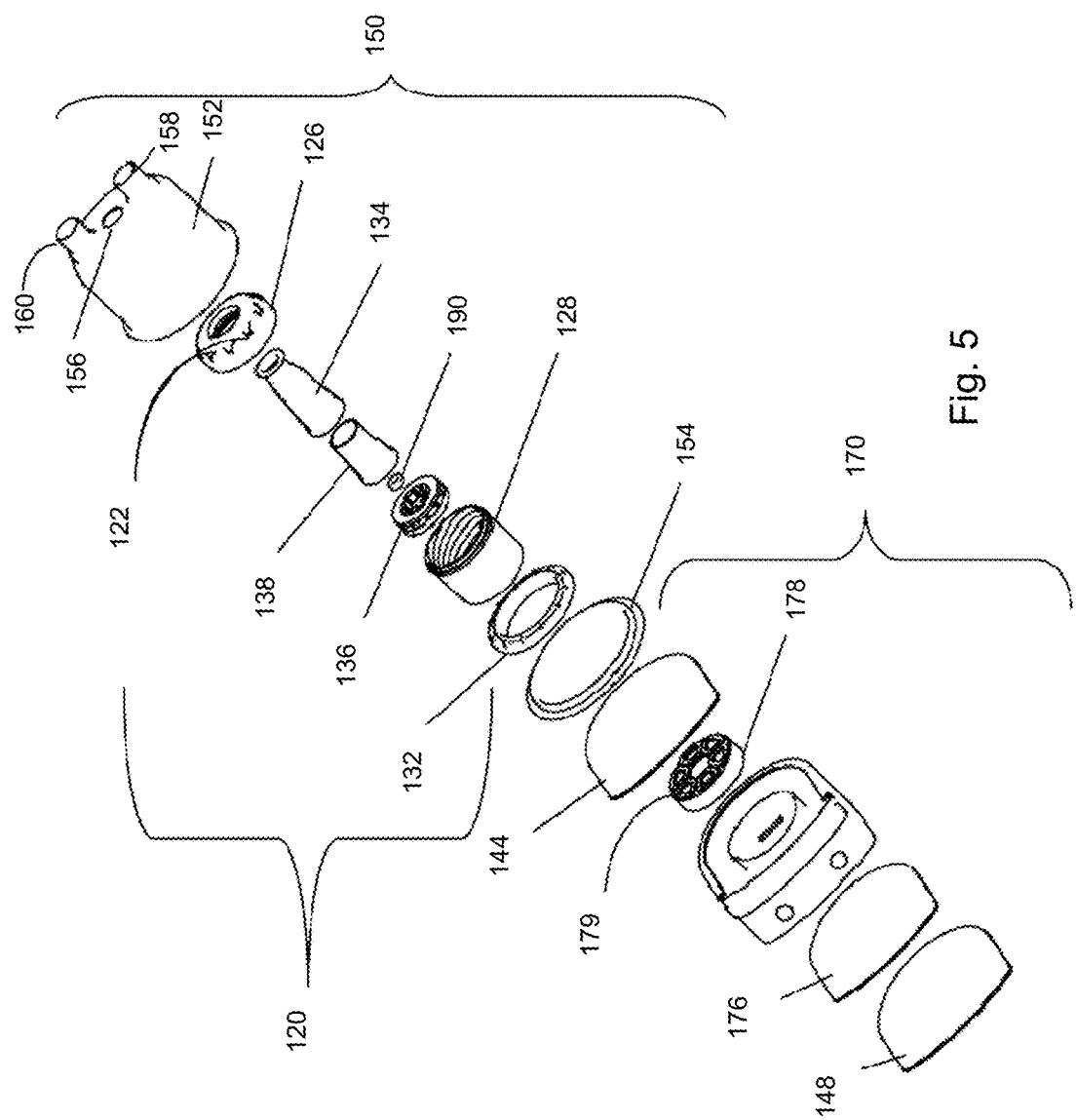
FIG. 5 is an exploded view of the apparatus of FIG. 2-4.

In certain embodiments, as illustrated in FIGS. 2-5, the base 170 also comprises a latch 172 configured to allow the insertion and removal of the chamber 150. The latch 172 may lift up or push down to enable the release or insertion of the chamber 150 from or to the base 170. In certain embodiments a retaining mechanism may be present in the base 170 to securely lock or retain the chamber 150 to the base 170 when coupled together. A lower portion of the chamber 150 may include a retaining rim 162, as illustrated in FIGS. 3-5, to facilitate the retention of the chamber 150 to the base 170. The base 170 may comprise a projection 163 configured to engage the retaining rim 162.

In certain other embodiments the retaining mechanism may include a spring (not shown) that biases the chamber 150 in contact with the base 170. In such an arrangement the latch 172 may enable the release of the spring to allow easier insertion or removal of the chamber unit. The retaining mechanism and latch 172 may include any arrangement as described for retaining a humidifier tub to the humidifier cradle in the co-owned pending U.S. patent application Ser. No. 11/988,870 entitled Humidifier and/or Flow generator for CPAP device filed 15 Aug. 2006 and published as US 2009/0194106 on 6 Aug. 2009, which is incorporated herein by reference in its entirety.

In certain embodiments (not shown) the base 170 may include a heater element, such as a filament heater element, ceramic heater element or other such heater element, arranged around or adjacent to the stator 178 to provide heating to the water 140 within the chamber 150. In other embodiments the stator 178 within the base 170 may provide induction heating to the water in the chamber 150 as described in more detail below.

Chamber

Referring to FIGS. 2-5, the chamber 150 includes a top portion 152 that is coupled to a bottom cover 154. The top portion 152 includes an air inlet 156, an outlet 158 and optionally a secondary inlet 160. The bottom cover 154 may include a retaining rim 162 to facilitate securing the chamber 150 to the base 170 as described above. In FIGS. 2-5 the top portion 152 forms a large tub-like configuration of the chamber 150 comprising the sides of the chamber 150 and the bottom cover 154 forms the bottom of the chamber 150. However, it is noted that the bottom cover 154 may be structured to form a lower portion of the chamber 150 rather than just the bottom of the chamber 150 (not shown). For example, the join between the top portion 152 and the bottom cover 154 may be located above the maximum water level 140 to reduce the potential of water leaks at any joins. The top portion 152 and bottom cover 154 may be permanently coupled during manufacturing for example by welding or gluing. Alternatively, the top portion 152 and bottom cover 154 may be removably coupled using a latch or catch mechanism such as clips, clamps or similar arrangement. For example using the latch mechanism as described for the reusable humidifier tub in the co-owned PCT application number PCT/AU2009/001232 filed 17 Sep. 2009, published as WO 2010/031126 on 25 Mar. 2010, the contents of which is incorporated herein in its entirety. A seal (not shown) may be provided between the top portion 152 and the bottom cover 154.

The chamber 150 may be constructed of plastic, aluminum or stainless steel or other such materials. In certain embodiments the chamber 150 may be constructed at least in part from a low melt material to prevent the chamber from being autoclaved and reused. Alternatively, the chamber may be constructed of material to allow for reuse of the chamber by autoclaving or other forms of cleaning or sterilization of the chamber 150.

As illustrated the chamber 150 may have a cylindrical cup-like or container configuration (see FIGS. 2-5). However, a person skilled in the art would understand that the chamber 150 may be constructed in any suitable shape, such as rectangular, square etc that facilitates supporting a blower 120 and retaining a supply of water.

The air inlet 156 provides a supply of ambient air to the blower 120 for pressurization. In certain embodiments the air inlet 156 (see FIGS. 3-5) may include a suspension tube 134 configured to suspend the blower 120 within the chamber 150. The suspension tube 134 may be constructed of a flexible material such as silicone. Alternatively the blower may be located within the chamber by other means as described in more detail below.

The chamber outlet 158 provides an outlet for the pressurized, and optionally, humidified air to exit the chamber 150. The chamber outlet 158 is configured to allow attachment of an air delivery conduit (not shown) to provide delivery of the pressurized air to a patient interface unit (not shown).

In certain embodiments the secondary inlet 160 may allow a supply of water to be provided to the chamber unit from a water reservoir (not shown). This facilitated the use of a smaller chamber 150 as the chamber would be required to only hold a small volume of water such as 1-100 ml, e.g. 1-50 ml, 1-20 ml, 1-10 ml. Small volumes of water may be heated faster than larger volumes of water, such as 300-500 ml or more. The water may be supplied to the secondary inlet 160 via in a continuous drip feed, bird feeding type configuration or using a pump or any other water delivery process. The secondary inlet 160 is sealed to prevent any leakage of pressurized air through the secondary inlet 160. The reservoir may include a bottle or water bag (not shown) that is arranged above or adjacent the secondary inlet 160.

The water may include sterile and/or filtered water. Alternatively, no water reservoir may be used and the chamber may be structured to hold the volume of water required for therapy or a therapy session.

In certain embodiments the secondary inlet 160 may be configured to provide a supply of a secondary gas such as oxygen to the breathable gas supply. Introducing the secondary gas into the chamber 150 may allow the secondary gas to be humidified together with the pressurized gas provided from the blower 120 prior to delivery to the patient. Alternatively a secondary gas may be provided at the air inlet 156. Such embodiments may provide for safer operation when used to introduce reactive gases, for example, oxygen into the respiratory system by isolating them from the electronic part of the system, thus reducing the risk of combustion initiated by an electric spark.

In certain embodiments the chamber may provide multiple secondary inlets 160 to allow the introduction of water and one or more secondary gases.

Pressure Generating Device or Blower

As illustrated in FIGS. 3-5, the chamber 150 is configured to receive a pressure generating device or blower 120. The blower 120 is arranged within the chamber 150 to pressurize a supply of air or gas supplied to the air inlet 156. The pressurized air or gas is then delivered to a blower outlet 122 for deliver within the chamber 150. The blower 120 has an outer housing that provides a barrier between the inside region of the blower 120 and the surrounding chamber 150.

In certain embodiments the blower 120 comprises an inlet flow path 138, an impeller 136 and a volute 128. The inlet flow path 138 is coupled to the air inlet 156 to direct the incoming air or gas to the impeller 136. The inlet flow path 138 may include one or more inlet vanes 142 (see FIGS. 3 & 4) adapted to direct the incoming air or gas flow towards the impeller 136. The inlet vanes 142 may be structure to direct the incoming air towards the impeller 136. The impeller 136 is driven to rotate by a drive mechanism to pressurize the incoming air or gas, explained in more detail below. The pressurized air or gas is directed from the impeller 136 to the volute 128, where it is directed to one or more blower outlets 122. The pressurized air or gas is then received from the one or more blower outlets 122 within the outer region of the chamber 150 where the pressurized air may be humidified if water 140 is present in the chamber 150.

In certain embodiments, as shown in FIG. 3-4, the air inlet 156 and suspension tube 134 of the blower may be coupled to the inlet flow path 138. The outer housing is formed by the assembly of an upper shroud 126, a volute 128 and a blower support 132. In certain embodiments the blower support 132 may be integrated with the volute 128 to reduce the number of parts for manufacturing. In certain other embodiments the upper shroud 126, volute 128 and blower support 132 may all be integrated into a single component as described in more detail below. In further other embodiments no blower support may be required, also described in more detail below.

In certain embodiments the inlet flow path 138 may be structured to retain a bearing 190, such as a ball bearing, within a hub of the impeller 136, the bearing 190 being configured to support the rotation of the impeller 136.

In certain embodiments an air bearing may be used to control the impeller 136, wherein the generated pressure acts to balance and lift the impeller. In certain other embodiments the impeller 136 may act as a passive magnetic bearing that is suspended within a magnetic field.

The volute 128 surrounds the impeller 136 to direct the air coming from the impeller 136. The volute 128 may include a plurality of stator vanes 146 designed to direct the air flow towards the one or more blower outlets 122. In certain embodiments the stator vanes 146 of the volute 128 may include a vortex structure adapted to direct the pressurized airflow in an upwards direction to the blower outlets 122. However, other vane structures may be utilized.

As illustrated in FIG. 4, the blower outlets 122 are located in the upper shroud 126 of the blower positioned near the top of the chamber. The blower outlets 122 may be adapted to direct the pressurized gas flow down towards water within the chamber 150 to facilitate humidification of the pressurized gas. In certain embodiments the one or more blower outlets 122 may include a one-way valve to allow the pressurized air or gas to exit the volute 128 but prevent water from entering into the blower 120. For example the blower outlets 122 may include a flexible membrane that is adapted to be expanded to open up the blower outlets 122 in use, i.e. when the impeller is rotating to produce a supply of pressurized air or gas. The expanded flexible membrane allows the supply of pressurized air or gas to flow out through the blower outlets 122. However, when the impeller is not rotating, the flexible membrane may close or cover the blower outlets 122 preventing passage through the blower outlets 122. Thus, the default position for the membrane in the non-active or standby mode of the apparatus, for example during transport, would prevent water from passing through the blower outlets 122 from the chamber 150 into the blower 120.

As the blower 120 includes only the rotating portions of the split motor configuration, described in more detail below, in certain embodiments the blower 120 may be configured to tolerate the presence of water. The presence of water within the blower may be tolerated due to the lack of electronics and controls within the chamber 150. The electronics and controls are separate to the rotating portion of the motor as they are located in the base 170.

Motor

Figure 12:
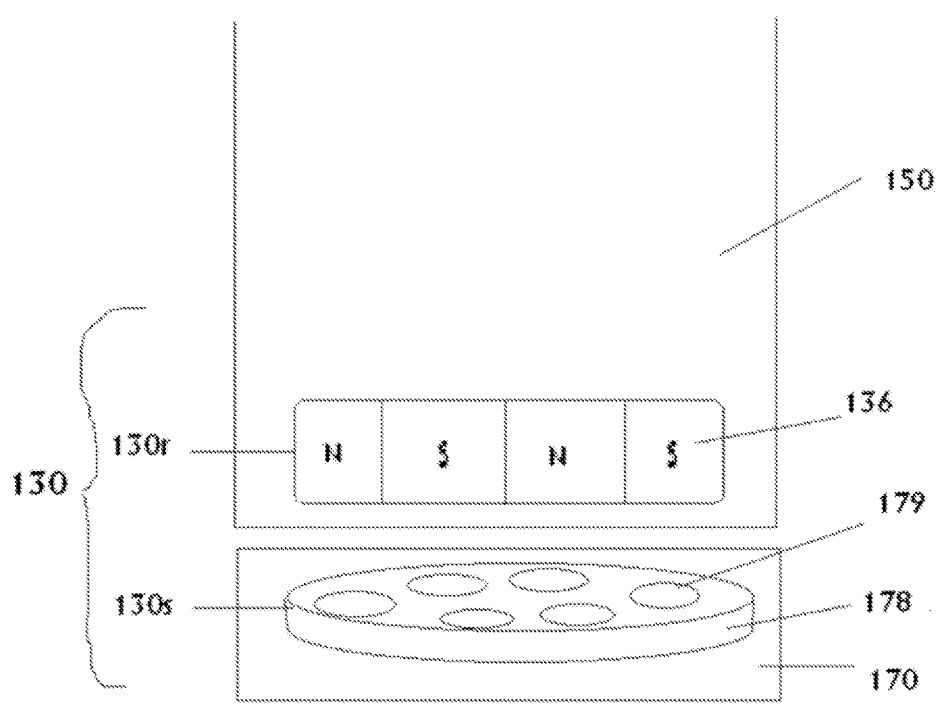
FIG. 12 is a schematic of an example split motor arrangement of the present technology.

A motor 130 drives the impeller 136 to rotate. In certain embodiments as shown in FIG. 12, the motor 130 is formed in a split configuration such that the stationary portion 130$s$ of the motor 130 is located within the base 170 and the rotating portion 130$r$ of the motor 130 is located in the chamber 150. In this arrangement the motor has a stacked or pancake construction in which the direction of the magnetic flux is axial, i.e. parallel to the axis of rotation. There is no direct coupling between the stationary portion 130$s$ and the rotating portion 130$r$, i.e. no shaft is coupled between the stationary component 130$s$ and the rotating component 130$r$ to drive the impeller 136. However, if required the impeller 136 may be configured to attach to a shaft (not shown) within the chamber 150.

Figure 14A:
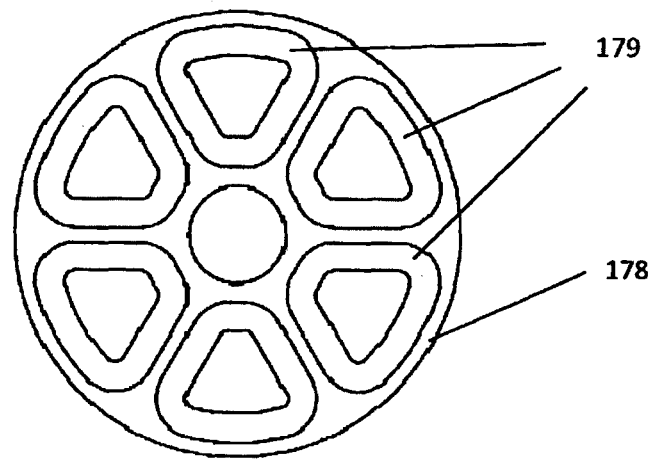
FIGS. 14a to 14c show various views of an exemplary stator with wound coils of the present technology.
Figure 14B:
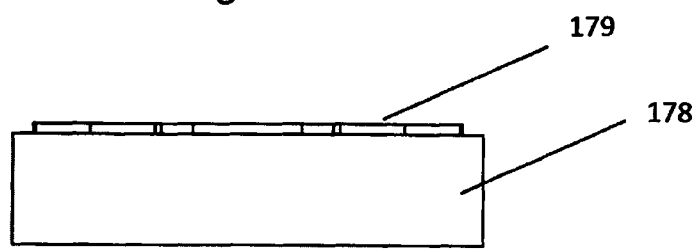
Figure 14C:
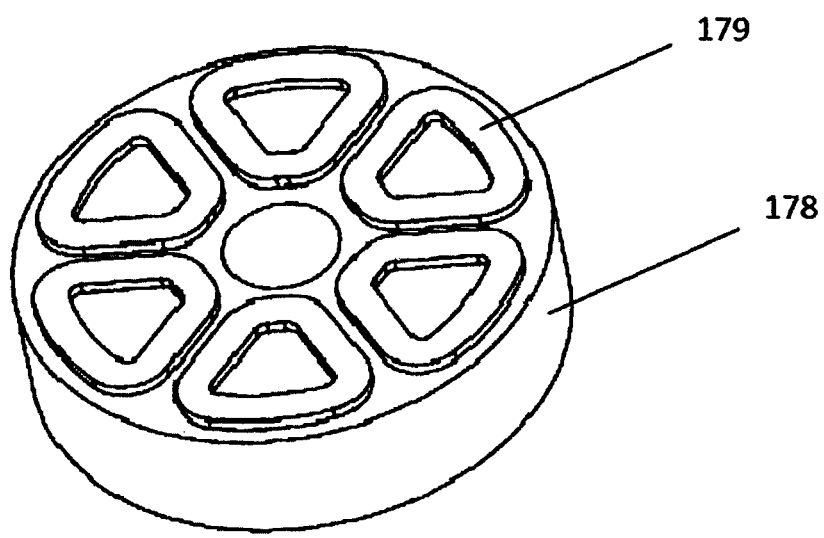
Figure 15A:
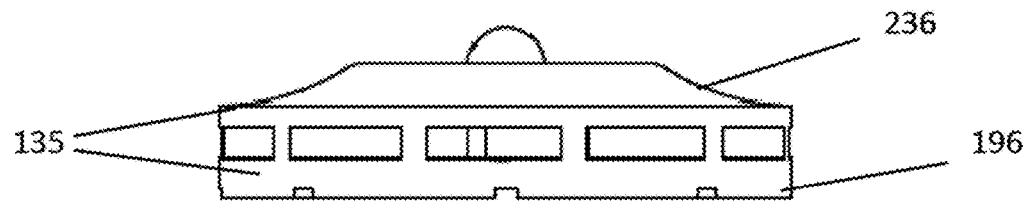
FIGS. 15a to 15d show various views of another exemplary impeller of the present technology.
Figure 15B:
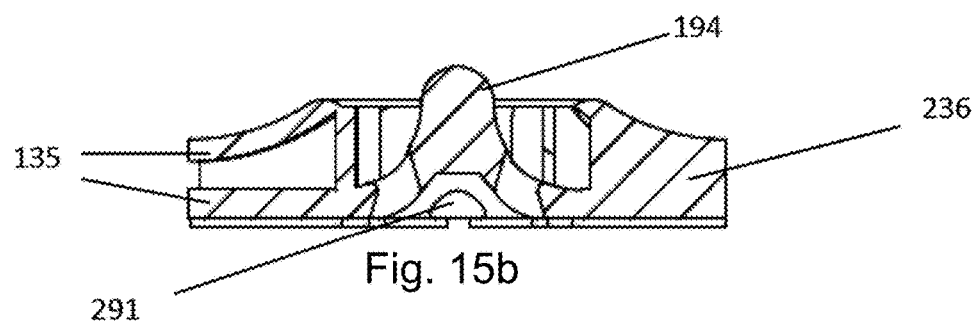
Figure 15C:
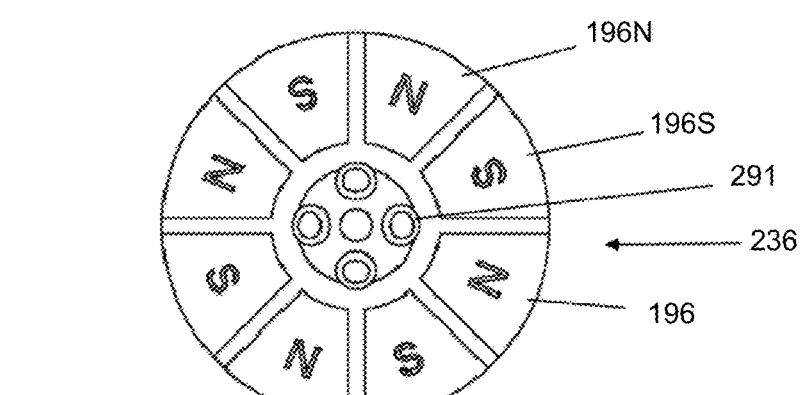
Figure 15D:
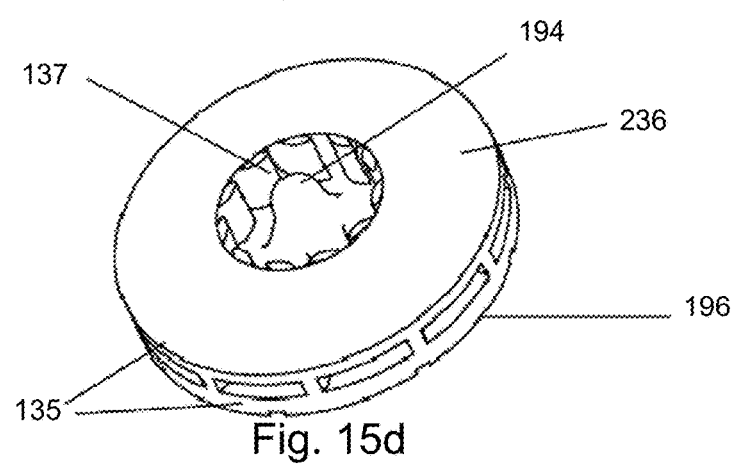

The stationary portion 130$s$ of the motor 130 includes a stator 178 having a plurality of wound coils 179 located thereon. FIGS. 14$a$ to 14$c$ illustrate a stator 178 having six wound coils 179 (i.e. three polar pairs) located thereon. The stator 178 includes a plurality of polar paired coils 179, such as 2-20 wound coils 179 such as 4, 6, 8, or 10 wound coils. The stator 178 and wound coils 179 are located in the base 170. The stator 178 with wound coil 179 may be located underneath the top cover of the base 170. The stator 178 may be embedded into a heat dissipating material for example by being molded into a heat dissipating plastic. Such a polymer material may include, for example, PA, PC, PP, PPS, PEEK and others depending on the addition of one or more fillers.

As shown the wound coils 179 are preferably arranged on one side of the stator in a stacked or pancake construction.

The stator 178 may include one or more sensors (not shown), such as hall sensor to sense the position of the magnet 196 on the impeller 136.

The rotating portion 130r of the motor includes the bearings 190 and a permanent magnet 196 coupled to or integrated with the impeller 136. The permanent magnet 196 includes a plurality of magnetized polar pairs (N, S) such as 2-20 magnetized poles, such as 2, 4, 6, 8, 10 poles (i.e. 1-10 polar pairs). Preferably a different number of poles are present in the magnet compared to the number of poles in the coils. For example, the stator may comprise 6 wound coils (i.e. 3 polar pairs) and the permanent magnet 196 may comprise 8 poles (i.e. 4 polar pairs). However, a person skilled in the art would understand that other arrangements may be utilized.

In certain embodiments the impeller 136 is comprised of magnetic material such that a separate magnet is not required, thus the impellers acts as both the permanent magnet 196 and the impeller 136. The impeller 136 is driven to rotate by the magnetic interaction of the magnet 196 coupled to or integrated with the impeller 136 with the electromagnetic drive supplied to the coils 179. The magnetic field produced by the coils 179 is conducted through the top cover of the base 170 and the bottom cover 154 of the chamber 150. The direction of the magnetic flux in this arrangement is axial. The distance between the stator 178 and the magnet 196 is minimized and is preferably less than 10 mm, such as about 8 mm, about 7 mm, about 6 mm, about 5 mm, about 4 mm, about 3 mm, about 2 mm, about 1 mm.

In certain embodiments the top cover of the base 170 and the bottom surface of the chamber 150 may be formed of a polymer such as a plastic, which is magnetically transparent to prevent interference with the magnetic flux path generated between the coils 179 and the magnet 196 on the impeller 136. In other embodiments the top cover of the base 170 and/or the bottom surface of the chamber 150 may be formed of a metallic material, such as stainless steel or aluminum such that the magnetic flux also heats one or both of these surfaces to assist in heating the water 140 in the chamber 150.

The stator 178 is coupled to a controller configured to control the motor. The controller may include a PCB 176, microprocessor and power supply for operation. The controller being adapted to electromagnetically control the coils 179 to facilitate the rotation of the rotating portions 130r including the impeller 136 within the blower 120 in the chamber 150. This arrangement isolates the air flow path from the electronic and control components of the apparatus. This may allow for replacement of the air flow path by simply replacing some or all parts of the chamber 150 and blower 120.

In certain other embodiments, not shown, the motor may have a more traditional cylindrical configuration having a shaft or rotor coupled to a magnet and driven to rotate by electromagnetic interaction between the magnet 196 and the coils 179. For example, a shaft or rotor may protrude from the bottom of the chamber 150 and insert into a portion of the base 170 to engage with the stator 178 and coils 179. The shaft may be coupled to a permanent magnet 196 that facilitates rotation of the shaft by electromagnetic interaction with coils 179. The shaft would also protrude into the chamber 150 and be coupled to the impeller 136. However, as in the embodiments described above the rotating portions 130r of the motor 130 are separate from the stationary portions 130s of the motor. The impeller 136, magnet 196 and shaft are located in the chamber 150 and the stator 178 with wound coils 179 is located in the base 170.

In certain embodiments the base 170 may be located above the chamber 150 and support the blower 120 within the chamber 150 such that the water 140 is located below the blower 120.

In certain other embodiment the motor may include a conduction motor arrangement such as a squirrel cage motor.

Impeller

Figure 13A:
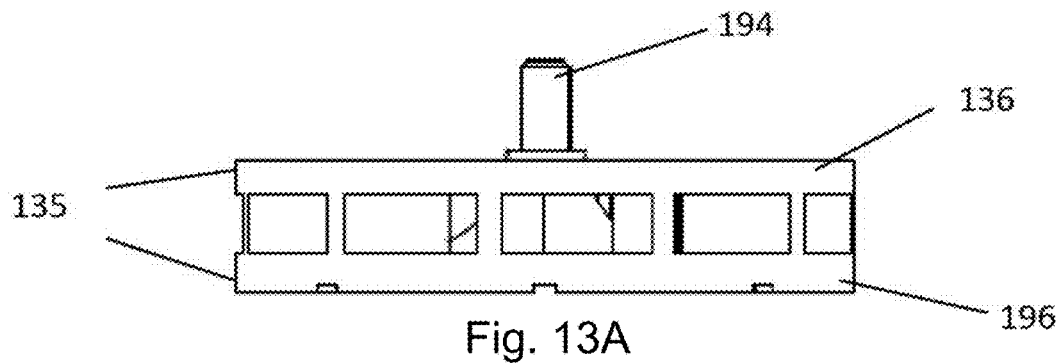
FIGS. 13a to 13c show various views of an exemplary impeller of the present technology.
Figure 13B:
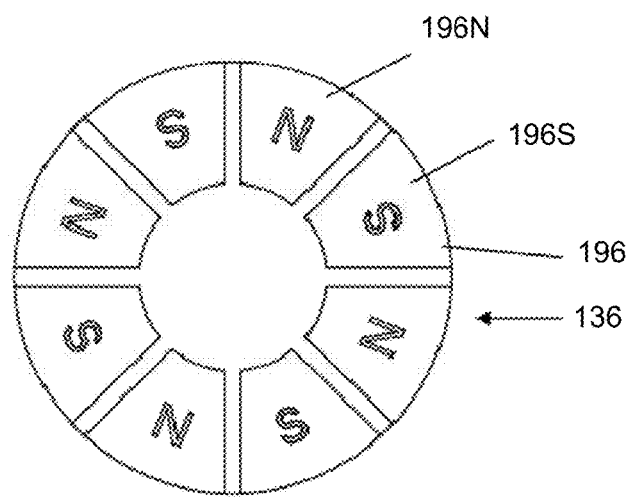
Figure 13C:
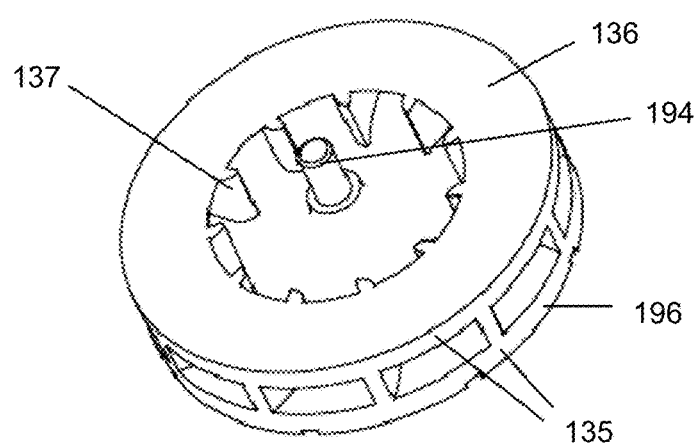

In certain embodiments the impeller 136 is magnetically conductive and may be formed from magnetic material, comprise a portion of magnetic material or be attached to a magnetic component to drive the magnetic rotation of the impeller 136. FIGS. 13a to 13c show an impeller 136 having the magnet 196 coupled to the bottom surface of the impeller 136. FIG. 13b illustrates the bottom view of an impeller 136 with the magnet 196 including eight magnetized poles (196N, 196S) that are arranged in polar pairs. It is to be understood that the magnetized impeller may comprise a different number of magnetized poles, e.g. 2-20 magnetized poles as discussed above.

The impeller 136 may be constructed of polypropylene, polycarbonate, polyamide or other suitable polymer material. In certain embodiments a magnetic material may be integrated or combined with the polypropylene, polycarbonate, polyamide or other suitable polymer material forming a magnetic polymer. The magnetic material may include magnetized ferrite, neodymium or other magnetic alloys. The impeller, or portions of it, may be formed of a polymer, such as an organic polymer, or other non-metallic magnet material. An example of such an impeller that may incorporate or consist of a plastic magnetic material or plastic magnet may be PANiCNQ or other combination of emeraldine-based polyaniline (PANi) and tetracyanoquinodimethane (TCNQ).

The impeller 136 may be a one piece molded construction, although other suitable materials and manufacturing techniques may be employed. The impeller 136 (see FIG. 13c) comprises a plurality of blades 137, 4-20 blades, such as 6-13 blades, that are sandwiched between a pair of disk like shrouds 135. The impeller 136 may include backward curved blades to improve the aero-dynamic centering of the impeller 136.

In an alternative configuration (not shown) the impeller 136, 236 may include an alternating shroud arrangement as described in pending U.S. patent application Ser. No. 12/083,350 filed 27 Oct. 2006 which is incorporated herein in its entirety. The impeller 136 may be a generally centrifugal impeller that accelerates the air in a generally tangentially direction. An impeller hub 194 may couple the impeller 136 with the bearings 190. In certain embodiments the impeller is independent, i.e. not directly coupled to the stator component of the motor, as described in more details below.

In certain embodiments the impeller 136 may be constructed to self-centre and self-balance in use by the formation of an air cushion that is formed in a gap between the rotating impeller 136 and the walls of the inlet flow path.

As illustrated in FIGS. 15a to 15d, in certain embodiments the impeller 236 may be constructed to facilitate the use of an air bearing. As above the impeller 236 may include a magnet 196 with a plurality of magnetized poles arranged in polar pairs (196N, 196S). The impeller may also include a plurality of apertures 291 adjacent the hub of the impeller that allow the air pressure to flow under the impeller and lift the impeller in use to form an air bearing arrangement. The pressurized air between the impeller 136 and the walls of the volute 128 may also assist in supporting the impeller 136.

In certain embodiments (not shown) the impeller may be configured to float on a small volume of water. A limited supply of water, may be provided to the blower 120 from the chamber 150. In such an arrangement the water may provide the lubricant to support the impeller 136 during rotation. The impeller may be a twin-side impeller.

In certain other embodiments the impeller 136 may act as a passive magnetic bearing that is suspended within a magnetic field.

In certain embodiments the impeller 136 may be constructed of a suitable material, such as a suitable magnetized material, such that eddy losses produced in the impeller may heat the impeller. The generated heat may be utilized to heat the airflow and/or the water.

In certain embodiments the blower 120 may comprise a plurality of impellers 136, 236 such as 2, 3 or more impellers that co-operate to provide a supply of pressurized air or gas.

Humidification

Pressurized air or gas within the chamber 150 may be humidified by a supply of water 140 within the chamber 150. The pressurized air or gas exits the blower 120 via the blower outlets 122 and enters the water containing area of the chamber 150 where humidification may occur. The water within the chamber 150 may optionally be heated. In certain embodiments the water may be heated by heat generated by the blower 120 being dissipated into the surrounding water 140.

In certain embodiments the base 170 may include a heating element configured to heat the water within the chamber 150. The heating element may include a ceramic heating element, filament heater or other such heating element. The heat is conducted through the top cover of the base 170 and into the chamber 150. The bottom cover 154 of the chamber 150 may be constructed at least in part from a heat conductive material.

In certain embodiment a heater may be provided within the chamber 150. For example, a heating filament or heating strip may be located within the chamber 150. The heating strip may be structured as described in co-pending U.S. patent application Ser. No. 12/669,889 which is incorporated herein in its entirety.

In certain embodiments the chamber 150 may be formed at least in part from a metal material such as steel, stainless steel or aluminum and the stator 178 with coils 179 located within the base 170 may be configured to provide induction heating to the water 140 in the chamber 150 as well as drive the rotating portions 130r of the motor. There may be some power losses for driving the impeller 136 due to the metallic interaction of the steel or aluminum with the coil 179 in the base 170. However, these losses may be gained as heat. In such arrangements when the chamber 150 is removed from the base 170 no heating would occur, thus improving the safety of the apparatus.

Furthermore, using such an arrangement may facilitate the recognition of the chamber 150 being engaged with the base 170, which may engage the control mechanism to allow the apparatus to be turned on. In other embodiments the chamber may be recognized by the base by other means such as radio frequency identification (RFID) tags or other recognitions systems, including those described in U.S. patent application Ser. No. 11/642,963 filed 21 Dec. 2006 incorporated herein in its entirety.

In certain embodiments the pressurized gas may not be humidified and no water is provided within the chamber 150.

In certain embodiments the chamber 150 may include sensors such as temperature and/or humidity sensors to measure the temperature and/or humidity of the air or gas within the chamber. A temperature sensor may be coupled to the heater element to assist in controlling the heating of the heater element and the temperature of the water 140 in the chamber 150.

Tapered Chamber Embodiment

Figure 6:
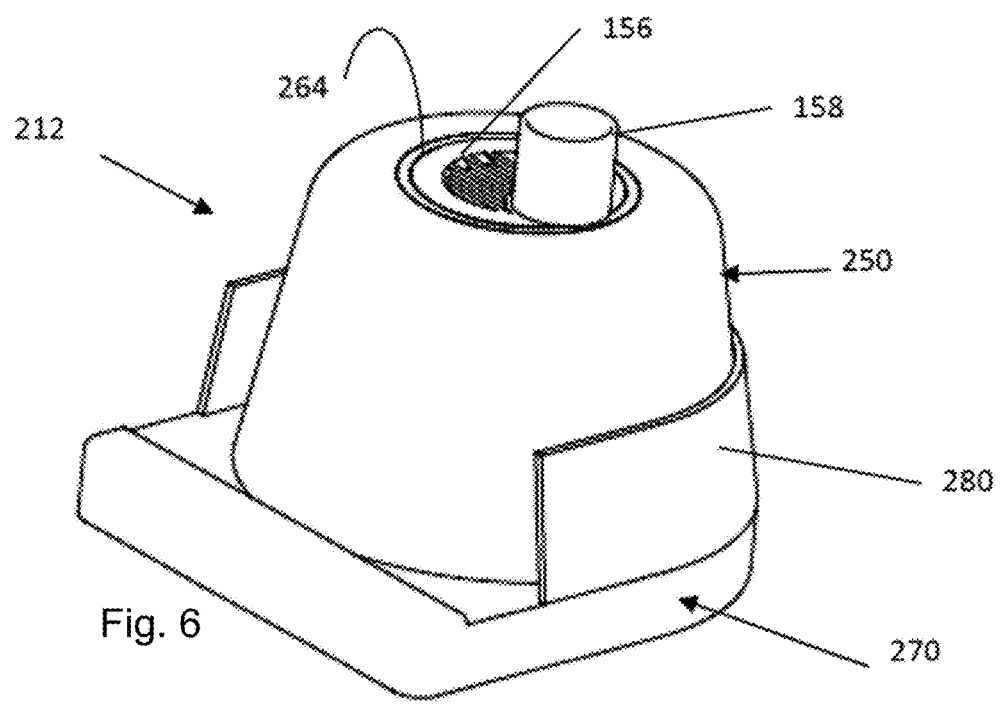
FIG. 6 is a perspective view of another example apparatus of the present technology.
Figure 7:
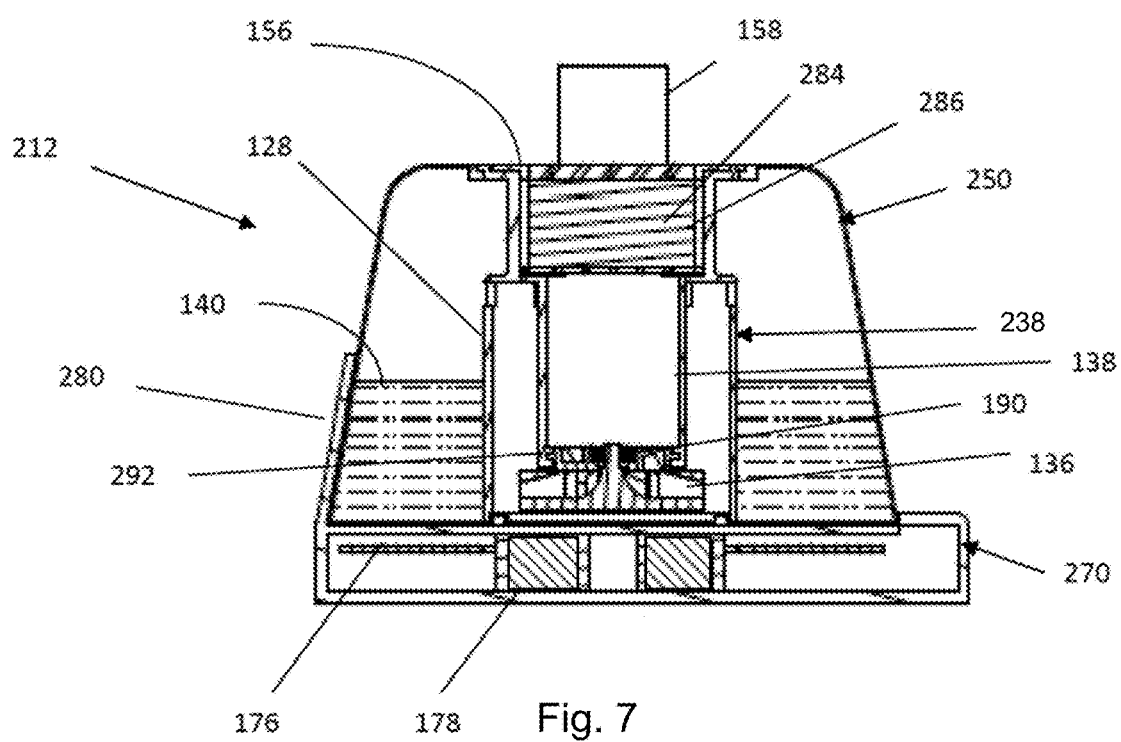
FIG. 7 is a cross-sectioned perspective view of the apparatus of FIG. 6.
Figure 8:
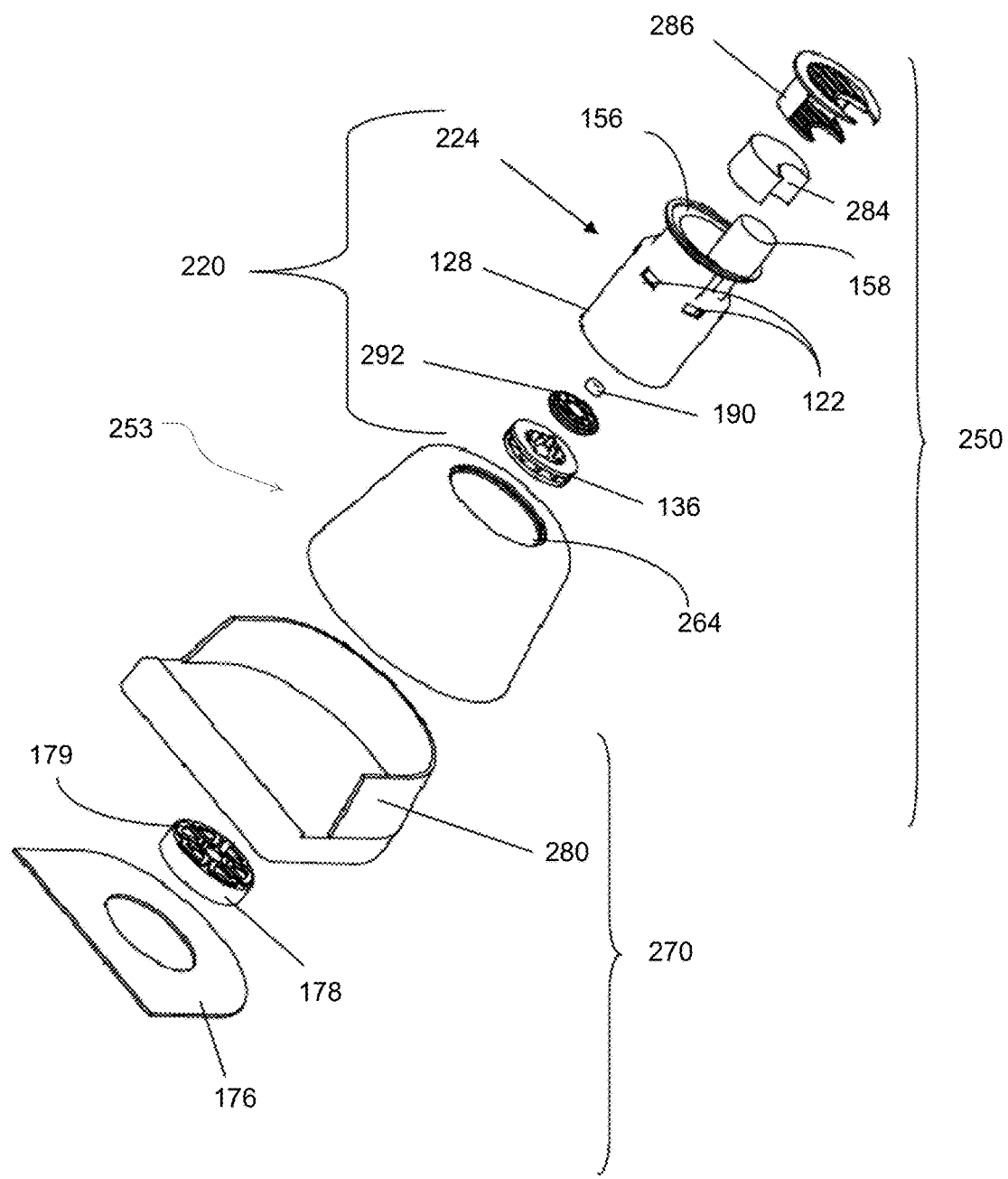
FIG. 8 is an exploded view of the apparatus of FIG. 6-7.

FIGS. 6-8 illustrate an apparatus 212 according to a certain embodiment of the technology having a tapered chamber 250. Similar to the embodiment above, the apparatus 212 includes a split motor configuration having a stator 178 with a plurality of wound coils 179 in a base 270 and a impeller 136 and blower 220 in a chamber 250. The chamber 250 is adapted to also hold a supply of water 140. For ease of understanding like variables are used to indicate similar components to those described in relation to the embodiment described above.

The chamber 250 may have a conical shape (see FIGS. 6-8) to facilitate the securing of the chamber 250 to the base 270. As illustrated in FIGS. 6-8, the base 270 may include a wall 280 that at least partially surrounds and supports the chamber 250 when inserted on to the base 270. An opening in the wall 280 would allow the removable slidable insertion of the chamber 250. The wall 280 may be angled inwardly to match a conical shape of the chamber 250 to prevent vertical release of the chamber 250. Thus, an angled wall 280 together with a conical shaped chamber 250 would secure the chamber 250 to the base once inserted.

In certain embodiments, not shown, the wall 280 may include a lip or protrusion that is engaged within a groove or channel within the side of the chamber 250 (not shown) to securely couple the chamber 250 to the base 270. Alternatively the chamber 250 may include the protrusion or lip and the wall 280 may include the complementary groove or channel structured to receive the protrusion or rim. The protrusion or lip may include a plurality of protrusions or lip portions or be a single continuous protrusion or lip around the wall 280 and/or chamber 250. Optionally, the base may contain a screw thread matching a screw thread on the chamber allowing the chamber to be screwed onto the base.

In certain embodiments, as illustrated in FIGS. 6-8, the chamber 250 may include an integrated top portion 152 and bottom cover 154 that are molded as a single integrated chamber component 253. For example the chamber component 253 may be molded in a cup-like configuration with an opening 264 at the upper surface. Thus, such a chamber would include a bottom wall and side wall(s). In such a configuration there may be no joins in the bottom of the chamber component 253 which reduces the risk of the water 140 leaking from the chamber 250. The opening 264 may be in the form of an aperture, see FIG. 6, configured at the top of the chamber component 253 to receive the blower arrangement 220 therethrough. In such an arrangement the air inlet 156 may be coupled to the blower 220 and received within a portion of the opening 264.

In certain embodiments the upper shroud, volute and blower support may be integrated into a single component, a volute insert 224, see FIG. 8. The volute insert 224 is inserted into the chamber 250. The volute insert 224 may be constructed as a molded insert. In certain embodiments the volute inserts 224 may be constructed at least in part from a flexible material such as silicone to facilitate vibration transfer from the impeller 136, 236 and reduce conducted noise.

In certain embodiments the bearing may be supported in a central portion of a vane and bearing housing 292 (see FIGS. 7-8). The vane and bearing support 292 is a stationary component that does not rotate with the bearings 190 or the impeller 136, 236. The vanes and bearing support 292 includes a plurality of stationary vanes that are adapted to direct the incoming air or gas to the impeller 136, 236. The vane and bearing housing 292 may be coupled to the inlet flow path 238 and may also provide vibrational support to the inlet flow path 238 to reduce conducted noise.

In certain embodiments an inlet filter 284 may be coupled to the air inlet 156 (see FIGS. 6-8). The inlet filter 284 is structured to filter the incoming air to remove particulate matter and/or viral and/or bacterial matter. The inlet filter 284 may be supported by a filter frame 286 that is received within the air inlet 156. The filter frame 286 may be coupled to the air inlet 156 for example using a bayonet connection, interference fit, snap-fit, press-fit or any other type of connection. As illustrate in FIGS. 6-8 the air inlet 156 may be formed in the volute insert 224.

In certain embodiments the chamber outlet 158 may be formed in the volute insert 224 (see FIGS. 6-8) and is received within the aperture 264 when the apparatus 212 is assembled.

Molded Blower Compartment Embodiment

Figure 9:
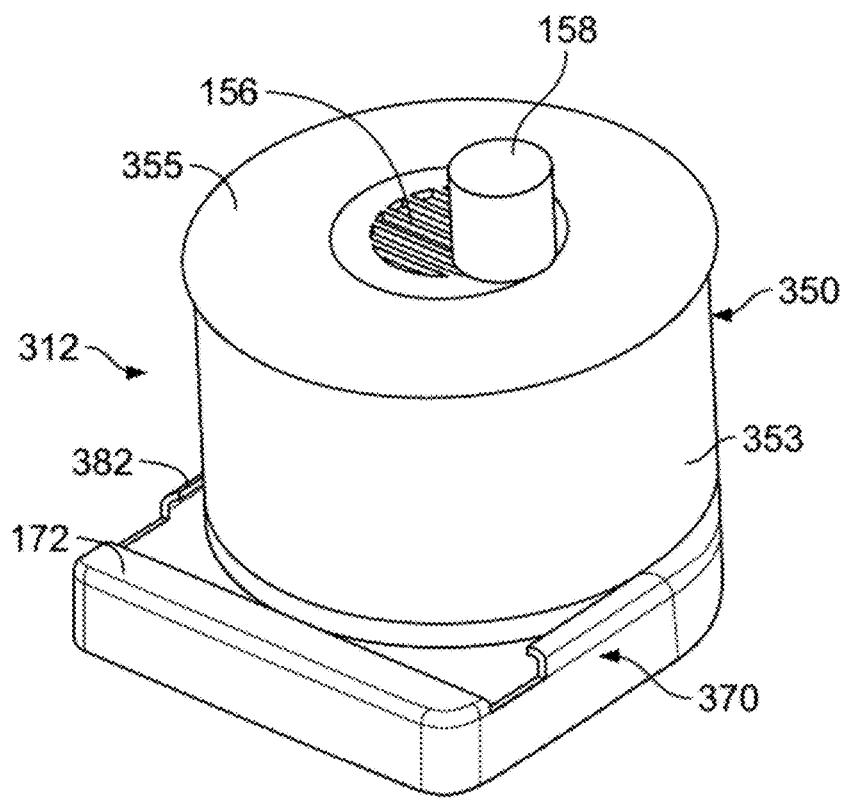
FIG. 9 is a perspective view of a further example apparatus of the present technology.
Figure 10:
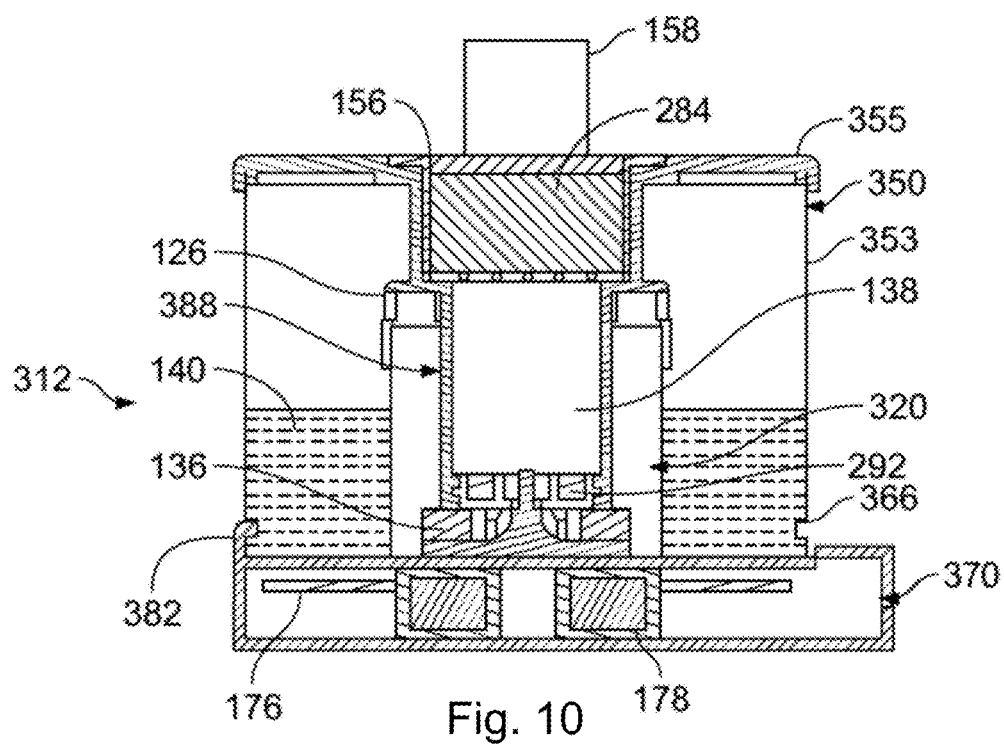
FIG. 10 is a cross-sectioned perspective view of the apparatus of FIG. 9.
Figure 11:
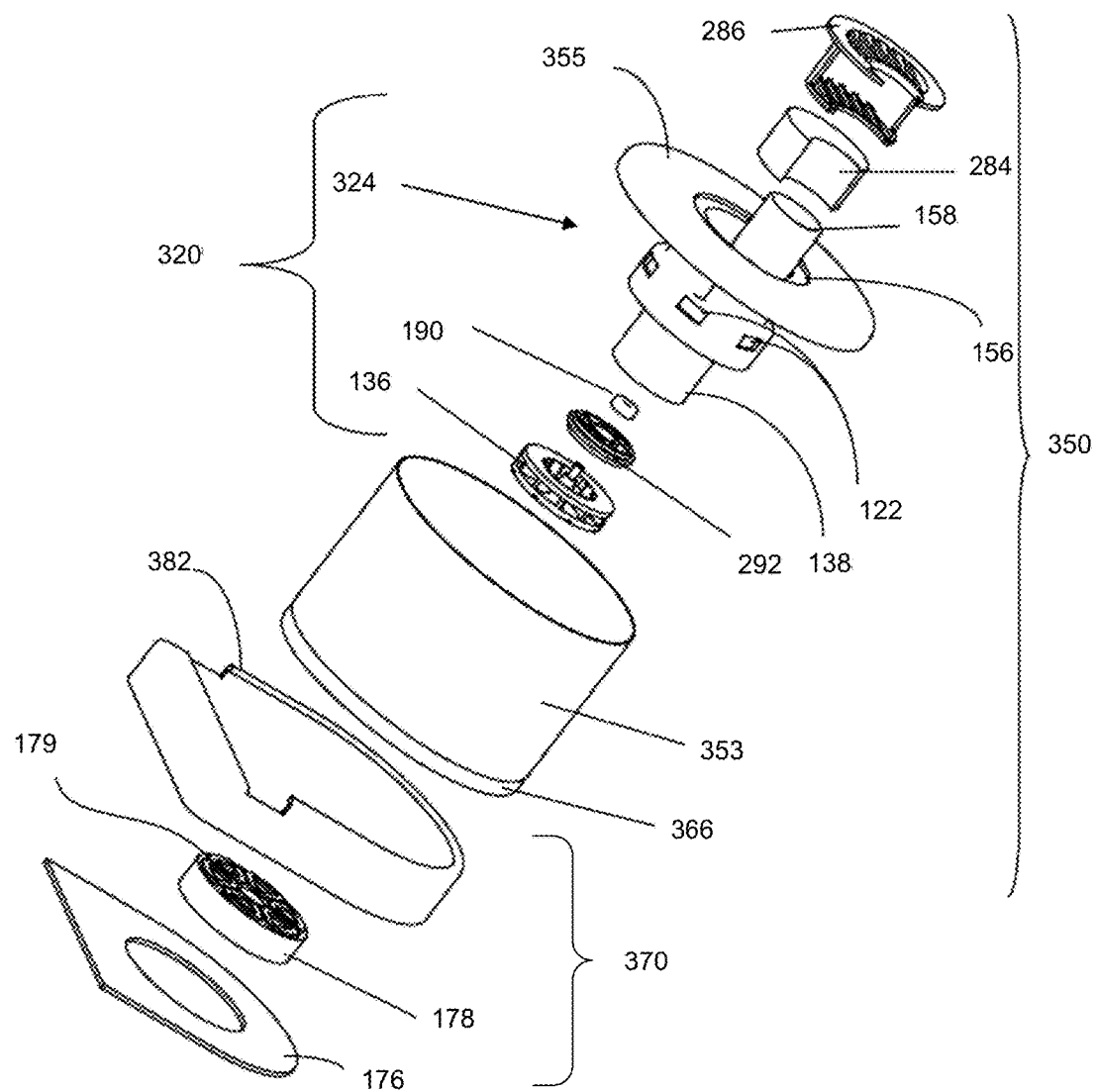
FIG. 11 is an exploded view of the apparatus of FIGS. 9-10.

FIGS. 9-11 illustrate an apparatus 312 according to a certain embodiment of the technology having a molded chamber 350 having a blower compartment 388. Similar to the embodiments above, the apparatus 312 includes a split motor configuration having a stator 178 with a plurality of wound coils 179 in a base 370 and an impeller 136 and blower 320 in a chamber 350. The chamber 350 is adapted to also hold a supply of water 140. Thus, the chamber may include a bottom and side walls to form a cup-like configuration. For ease of understanding like variables are used to indicate similar components to those described in relation to the embodiment described above.

As illustrated in FIG. 10 the chamber 350 includes a blower compartment 388 that is molded into the bottom of a chamber 350. The blower compartment 388 forms an open cylinder or hub within the chamber 350 that is configured to receive the blower 320 therein and forms an outer housing of the blower 320. Although illustrated as a cylinder, the blower compartment 388 may have other configurations configured to house the blower 320 within the chamber 350. The blower compartment 388 may form the volute 128 and result in no blower support being required.

As with the tapered chamber 250 described above, the chamber 350 may have an integrated chamber component 353 such that the chamber component 353 may be formed as an open container, (such as an open cylinder). In this arrangement the opening 264 may result in the top portion of the chamber component 353 being open, see FIG. 9, and a chamber lid 355 being coupled to the chamber component 353. The chamber lid 355 may sealingly couple to the blower 320 to align the blower 320 within the chamber 350 when the lid 355 is inserted over the chamber component 353. In certain embodiments some components of the blower 320, such as the inlet flow path 138, volute 128 and upper shroud 126, may be integrated into a volute insert 324 that is inserted into the blower compartment 388. The volute insert 324 may be integrated with the chamber lid 355 (see FIG. 11). A reduction in the number of components may facilitate easier assembly and manufacturability of the apparatus 312.

The chamber 350 may be coupled to the base 370 in a similar manner to that described above. In certain other embodiments, see FIGS. 10-11, the chamber 350 may include a channel 366 that is configured to receive a flange 382 on the base 370 for retention of the chamber 350 to the base 370.

The volute insert 324 may also include an inlet filter 284 and filter frame 286 in a similar arrangement to that described above.

Radial Control Arrangements

Figure 16A:
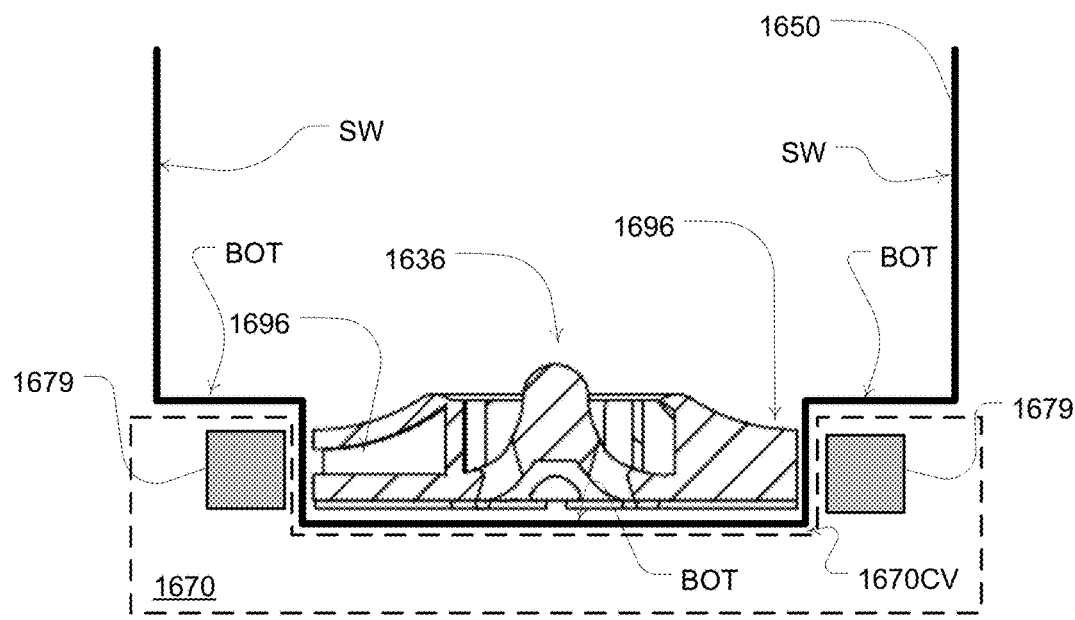
FIG. 16a is a side view cross sectional illustration of components of an embodiment of the present technology with an impeller and coils configured in a radial control arrangement, with a cross section of the chamber taken along line SV of FIG. 16b.
Figure 16B:
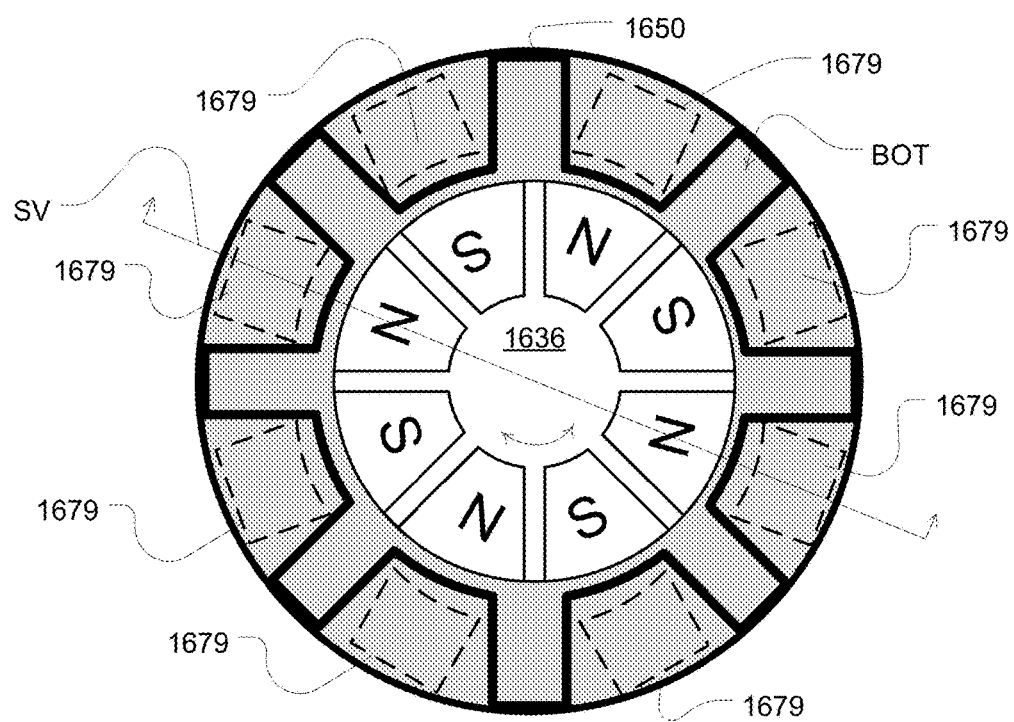

In the embodiments of FIGS. 16-17, the split design of the stator and rotor elements of the motor of the blower may be configured in a radial control arrangement, rather than a stacked arrangement of the previously described embodiments. For example, as illustrated in FIGS. 16a and 16b, the impeller 1636 may be placed or inserted within a chamber 1650 having a cup-like, bottle or container configuration. Optionally, a bearing (not shown) may also contact a bottom of the chamber to promote rotation of the impeller with respect to the chamber. The chamber 1650 will include a bottom (labeled BOT) and one or more side walls (labeled SW) that will permit the container to hold water (as well as the impeller) and thereby permit a simplified re-filling of the humidification chamber when the container is lifted (with the impeller) and removed from the base 1670 and the coils.

The impeller 1636 may include magnets 1696. When inserted in the bottom of the chamber, coils 1679 are located radially outward of the magnets such that they permit a radial control of the rotational movement of the impeller that will generate a pressurized airflow from the chamber. In this embodiment, the coils may be located within a housing, shell or cover of the base 1670. A bottom BOT of the chamber may fit into a cavity 1670CV, such as a cylindrical cavity, formed by the base such that a bottom portion of the chamber may be inserted into the cavity of the base. Thus, the magnetic field generated from the coils to control movement of the impeller may traverse a wall of the structure of the chamber and may also traverse a cover or wall of the housing of the base that separate the coil and magnetic control elements. Although not shown in FIG. 16a, the embodiment will include an air inlet that may be formed with a volute insert 224 as well as any suitable outlet such as previously described. Similarly, although not shown in FIG. 16a, in some embodiments additional coils may be added below the impeller such that the coils of the base and the magnetic impeller may be arranged in a combined radial and stacked control arrangement.

Figure 17A:
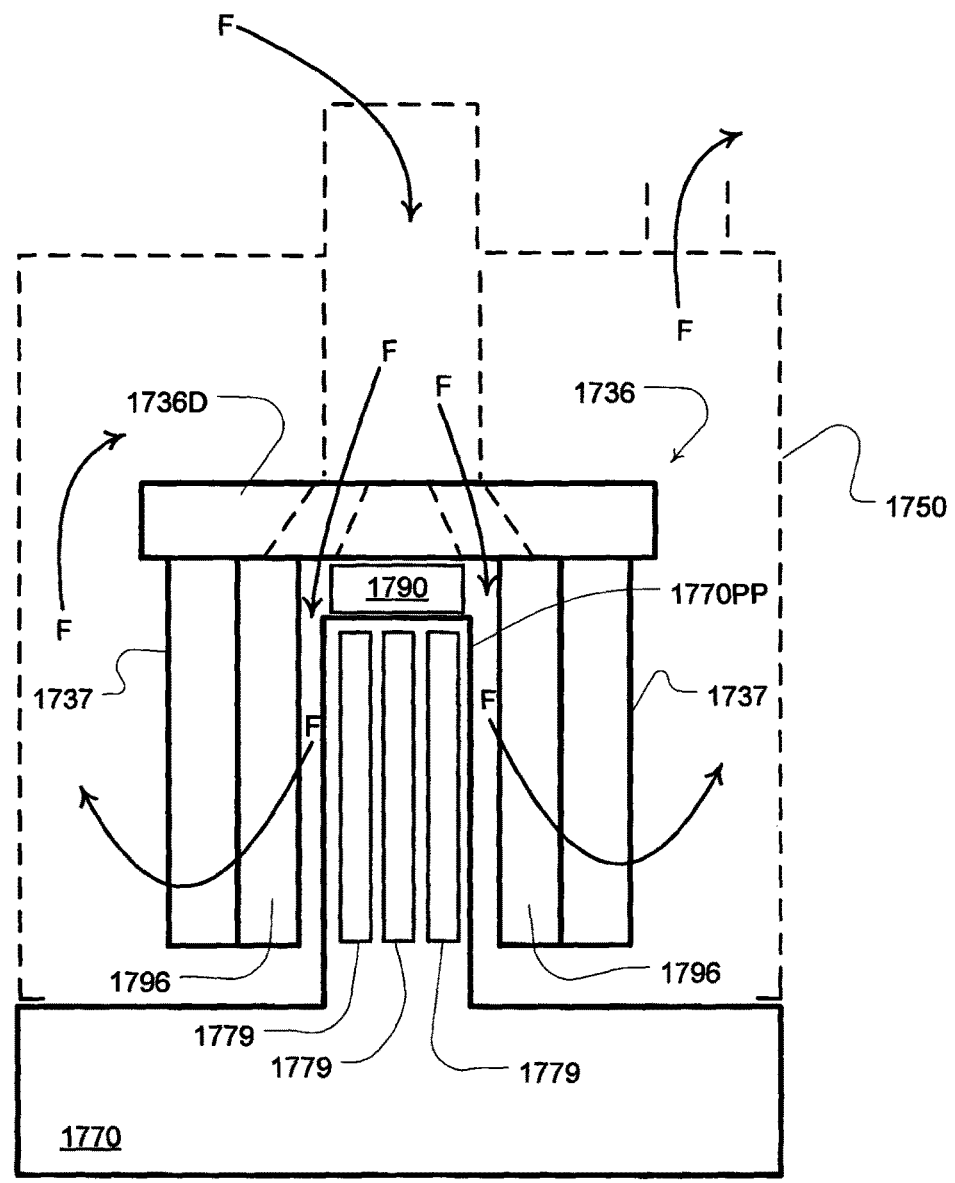
FIGS. 17a and 17b show side view illustrations of components of additional embodiments of the present technology having impeller and coil configurations in a radial control arrangement.
Figure 17B:
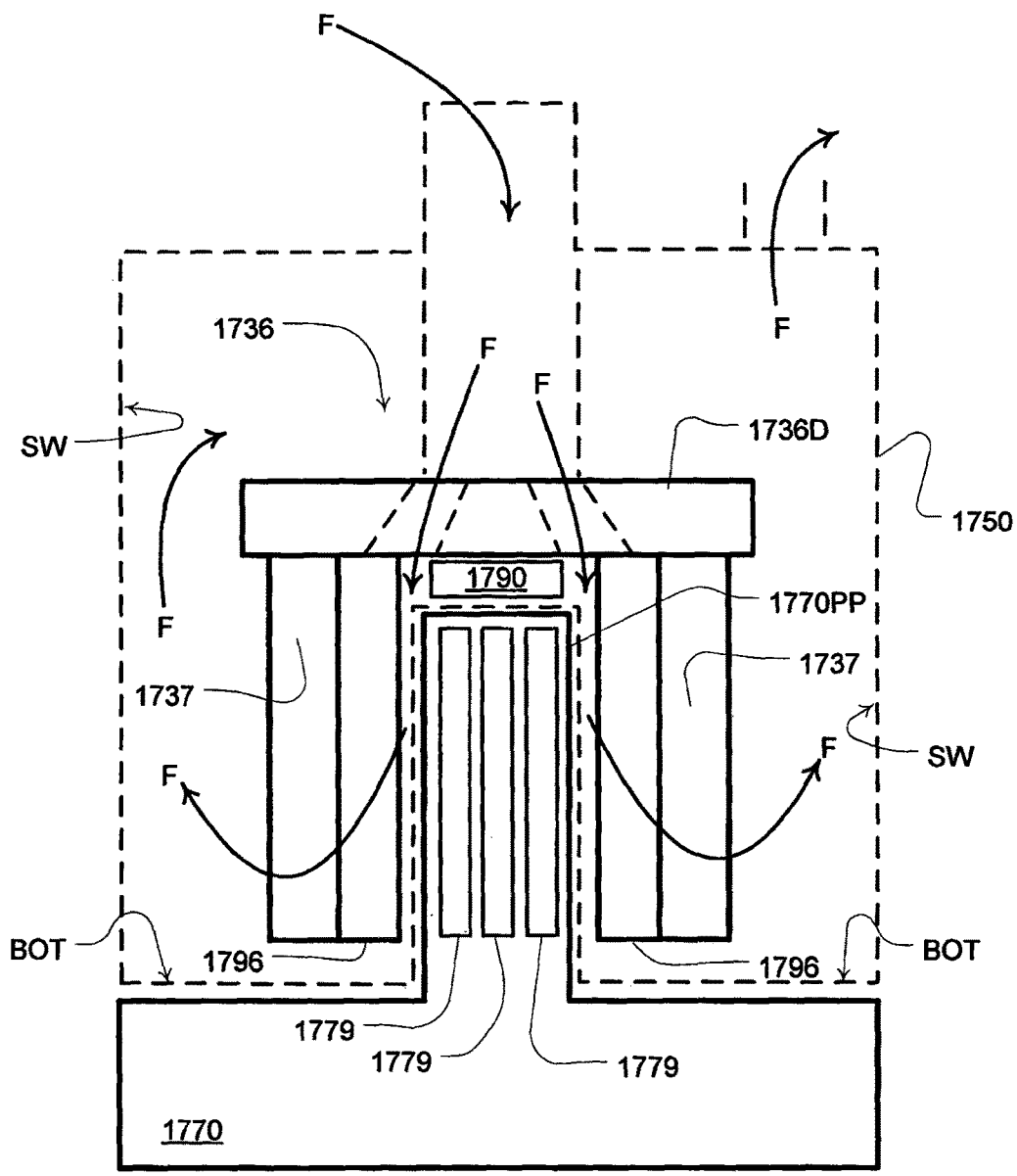

In another radial control embodiment shown in FIGS. 17a and 17b, the impeller includes vertically extending blades 1737 for air movement. The blades 1737 may extend downward from a disk portion 1736D of the impeller. Although two blades are shown in FIGS. 17a and 17b, additional blades may be implemented about the disk. The blades may include magnetic or magnet portions 1796. The impeller may rest on or include a bearing 1790 to permit rotation with respect to the structure of the base 1770 and chamber 1750. The base may include a centrally extending (e.g., rising) pedestal portion 1770PP, which may be a cylindrical shape. The extending pedestal portion may serve as a central support for rotation of the disk portion of the impeller and/or its bearing. In this regard, the impeller 1736 may be arranged such that the blades of the impeller rotate around the perimeter of a cylindrical pedestal portion 1770PP while the disk pivots at a top surface of the pedestal portion. To control the rotation of the impeller with respect to the base, the pedestal portion 1170PP of the base may serve as a housing for one or more coils 1779. Thus, when assembled for operational use, the magnets of the impeller are located radially outward of the coils. Although not shown in detail in FIGS. 17a and 17b, the embodiment will include an air inlet that may be formed with any volute insert 224 as well as any suitable outlet such as previously described.

In the embodiment of FIG. 17*a*, the chamber 1750 is formed as a cylinder (e.g., without a bottom wall) such that fluid for humidification may be in direct contact with a housing of the base 1770. In this regard, a seal may be applied at a side wall contact portion where the chamber meets the base and the sealing of the chamber 1750 with the base permits the chamber and base combination to serve as a water container. However, in the embodiment of FIG. 17*b*, such a seal may not be required. In FIG. 17*b*, the chamber 1750, similar to the embodiment of FIG. 16*a*, is formed in a bottle or container configuration. Thus, the chamber will include a bottom BOT to permit it to retain water for humidification. The chamber will typically include an opening (e.g. near the top of the chamber) to permit insertion of the impeller 1736 into the chamber. The impeller may then be respond to the coils for operation of the blower when the chamber is placed in the base 1770.

Generally, the features of radial embodiments of the respiratory apparatus just described differ from the stacked embodiments of the respiratory apparatus in the relative structural locations of the stator and the rotor. However, all of the other features of these embodiments may be interchanged such that any of the features of the stacked embodiments may be implemented in the radial embodiments. Similarly, any of the features of the radial embodiments may be implemented in the stacked embodiments. Merely by way of example, the radial arrangement may implement the features relating to tapering, tapered chamber, blower compartment, sensors, impeller material (e.g., formed of magnetic material) etc. as previously described.

Spiral Flow Paths

Figure 18A:
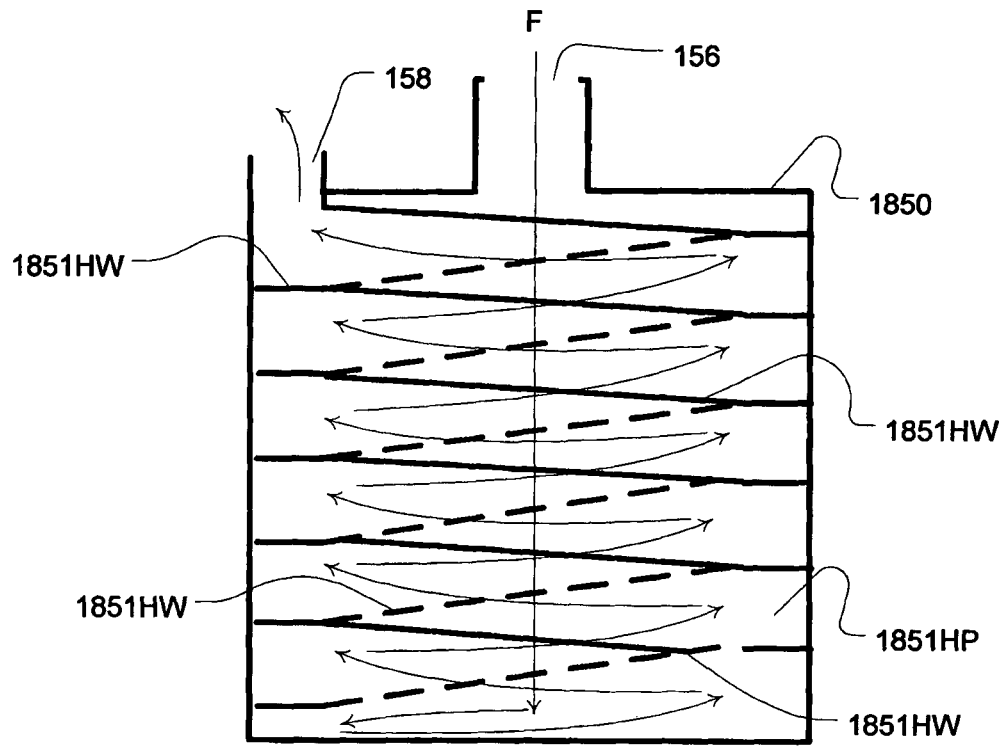
FIG. 18a is a side view illustration of an example humidifier chamber in some embodiments of the present technology implementing a spiral pathway.
Figure 18B:
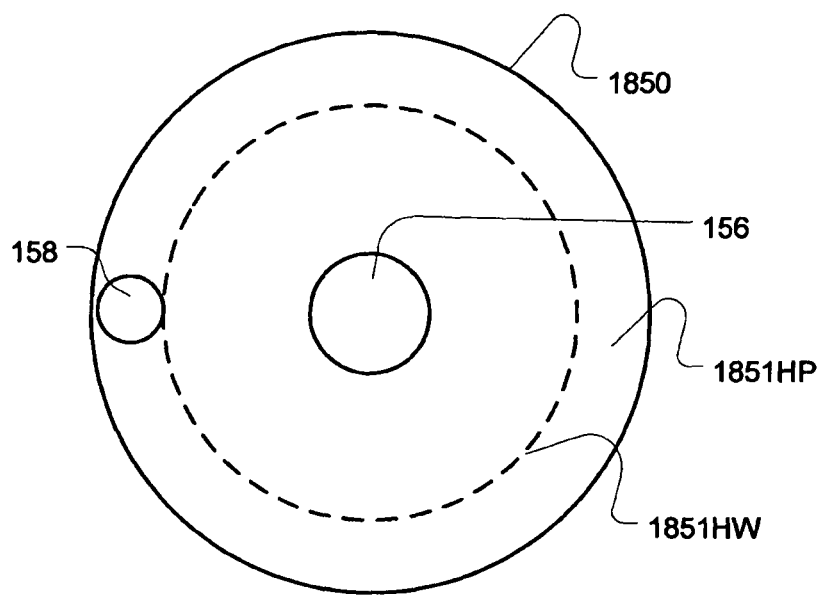

In some embodiments, the chamber may be configured with a spiral flow path, such as in a helical flow configuration, for the air flow from the impeller through the chamber. One such spiral pathway 1851HP example is illustrated in the chamber 1850 illustrated in FIGS. 18*a* and 18*b*. For example, internal spiral wall(s) 1851HW may be arranged to spiral around the internal periphery of a cylindrical side wall of the chamber (and around the impeller area) to spirally guide the pressurized flow of air around and upward within the chamber to the outlet 158 at the top of the chamber. This pathway around the chamber serves to increase the distance that the airflow may travel in the humidification chamber. The increase may permit the flow of air to have a greater surface contact with the water of the humidification chamber to more efficiently enable humidification of the pressurized air. It is noted that FIG. 18*a* does not show the blower compartment, impeller or volute components for pressurized air flow generation. However, the chamber may be implemented with any of the blower and humidifier embodiments previously described such that the airflow pathway spirally circumscribes the blower components within the chamber. In such versions, a blower compartment or volute may expel the airflow from the blower or impeller into the spiral pathway proximate to the bottom of the chamber. The spiral flow pathway may then be configured to deliver the pressurized air to an air outlet proximate the top of the chamber. Optionally, in some embodiments, the spiral wall(s) may include a spiral heating element that extends along the pathway formed by the spiral wall to heat the water and air of the spiral pathway.

Figure 19A:
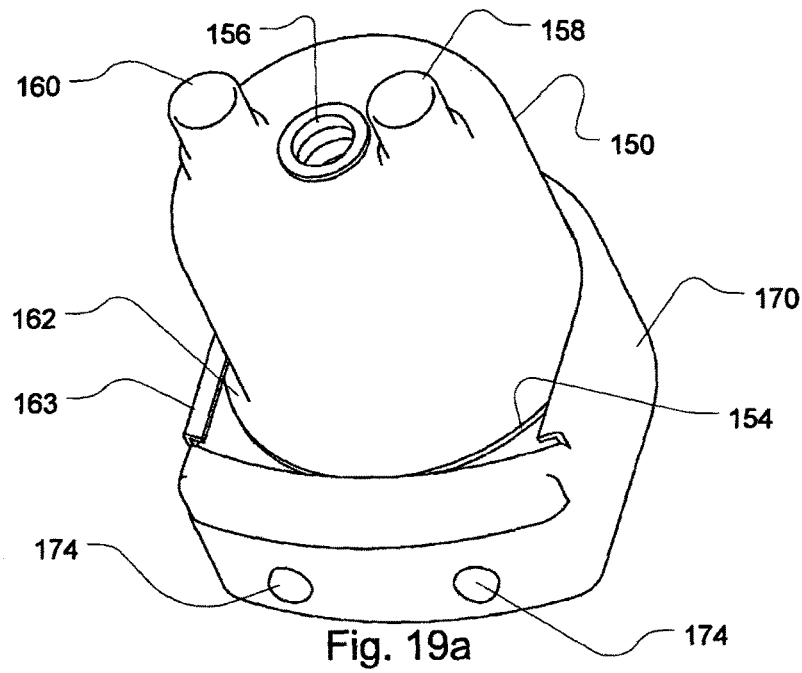
FIG. 19a is an illustration of an embodiment of the present respiratory apparatus technology with spiral flow technology.
Figure 19B:
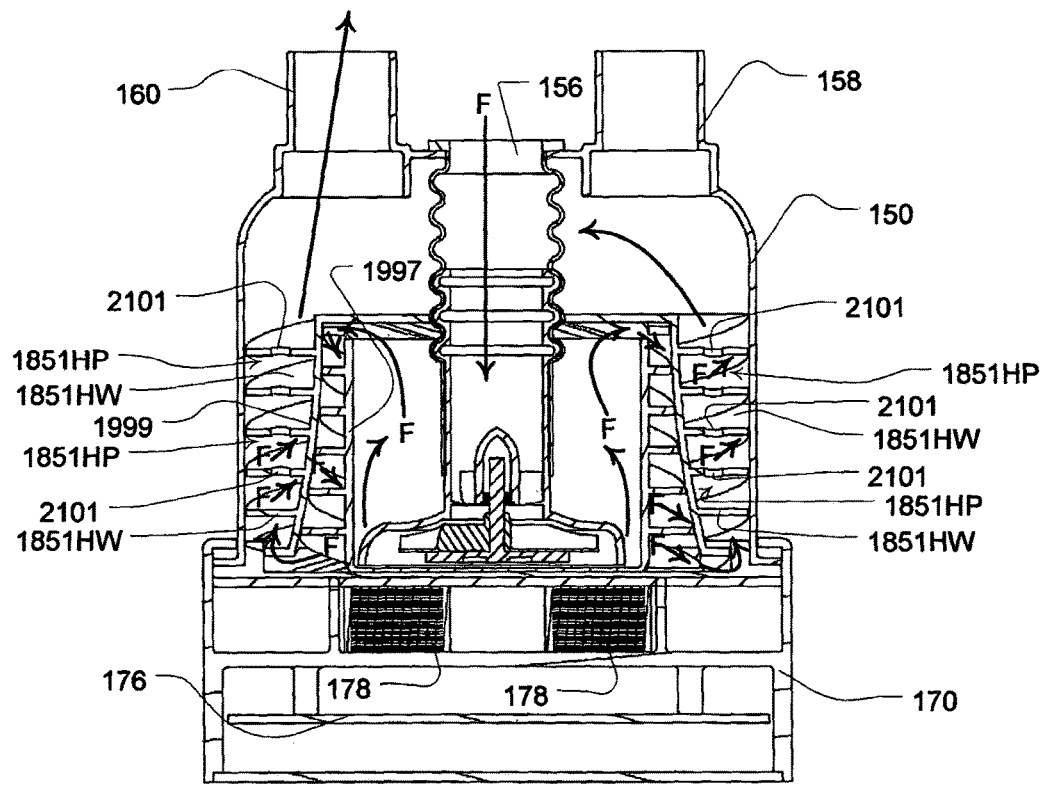
FIG. 19b is a cross sectional view of the embodiment of FIG. 19a showing helical humidification pathways.
Figure 19C:
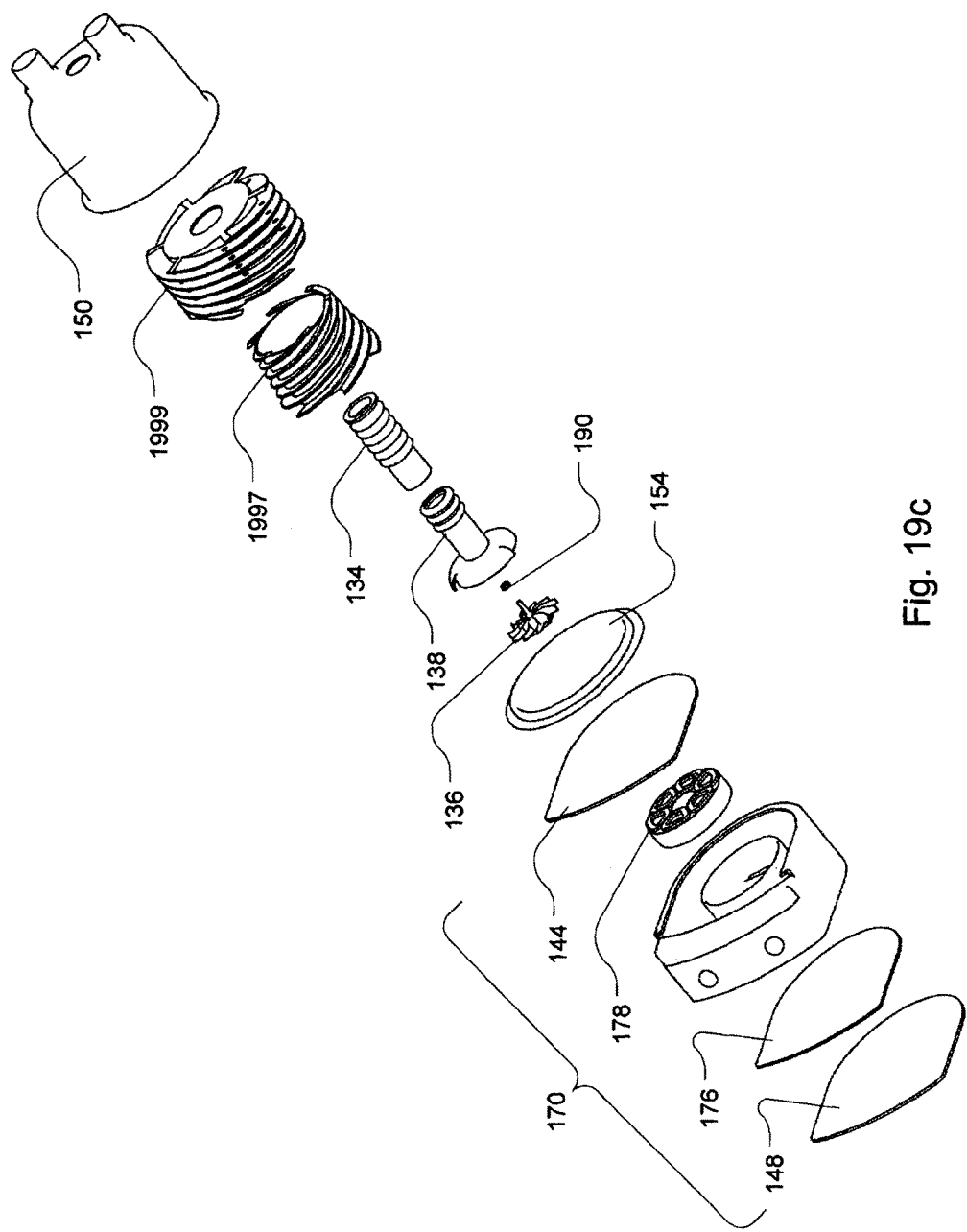
FIG. 19c is an exploded view of the components of the embodiment of FIG. 19a, including a spiral volute and a spiral humidification flow insert.
Figure 20A:
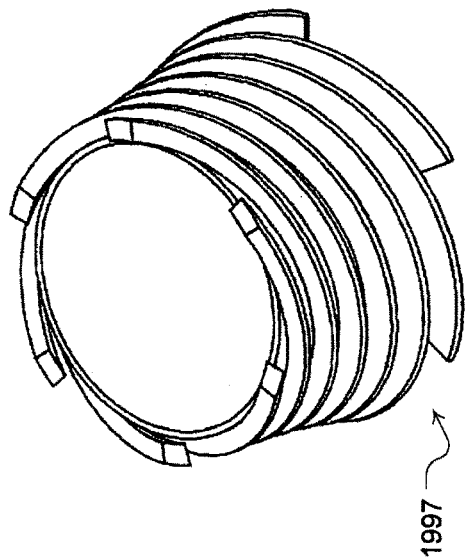
FIGS. 20a to 20c are views (perspective, top plan and front view respectively) of an example spiral volute in some embodiments.
Figure 20B:
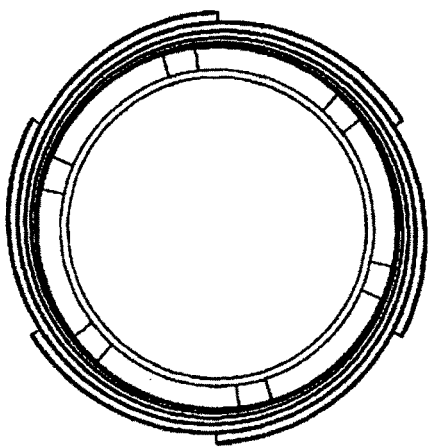
Figure 20C:
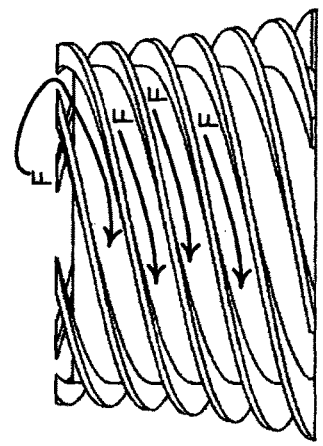

An embodiment of such an apparatus with spiral flow pathways may be further considered in view of FIGS. 19 through 21. This embodiment is similar to the embodiment of FIG. 2 and utilizes similar components as described with reference to FIG. 2. However, in this embodiment, flow path inserts configured with helical walls to form spiral pathways for the flow from the blower are implemented. As seen in FIGS. 19*c*, 19*b*, 21*a*, 21*b* and 21*c*, a humidification flow insert 1999 may be assembled within the chamber 150. The spiral humidification flow insert 1999 includes spiral walls 1851HW that, in this embodiment, form helical pathways for the air flow from the impeller. Optionally, the spiral walls may include one or more wall aperture(s) 2101 to permit a vertical transfer of fluid or air from one pathway to another.

The embodiment of FIGS. 19 through 21 also employs an optional insertable spiral volute 1997 to direct the rising air flow (labeled with arrows F in the figures) from the impeller of the blower. Similar to the flow insert 1999, the spiral volute includes spiral pathways in a helical configuration on an outside of the spiral volute but may also include such a configuration on an inside of the spiral volute. Thus, the spiral volute may be arranged to direct the rising flow of air inside the volute, which may have a spiral rise from the impeller, in a downward helical direction on the outside of the volute, to a bottom of the spiral humidification insert 1999 (best seen in FIG. 19*b*). Upon exiting the bottom outside of the flow paths of the spiral volute 1997, the flow will then enter the spiral humidification flow insert 1999 to then rise helically toward the outlet 158.

Noise Reduction Components

Any of the embodiments of the present technology discussed herein may include additional optional components to further reduce operational noise of the blower. For example, as previously described a filter may be implemented at the inlet of the blower. In some versions, a foam filter may be implemented around the impeller or its vanes such as locating a filter within the volute 128. In some embodiments, a biasing component, such as a spring, may be included within the blower compartment to stabilize or minimize vibration of the impeller and potentially further reducing noise. For example, in the embodiment of FIG. 4, a central spring may be included within the inlet flow path 138 to ply a downward resilient force against the bearing 190. In some embodiments, the coils may be removed from the PCB and attached by wire leads so that they may be mounted in a manner to reduce coil vibration.

Figure 22:
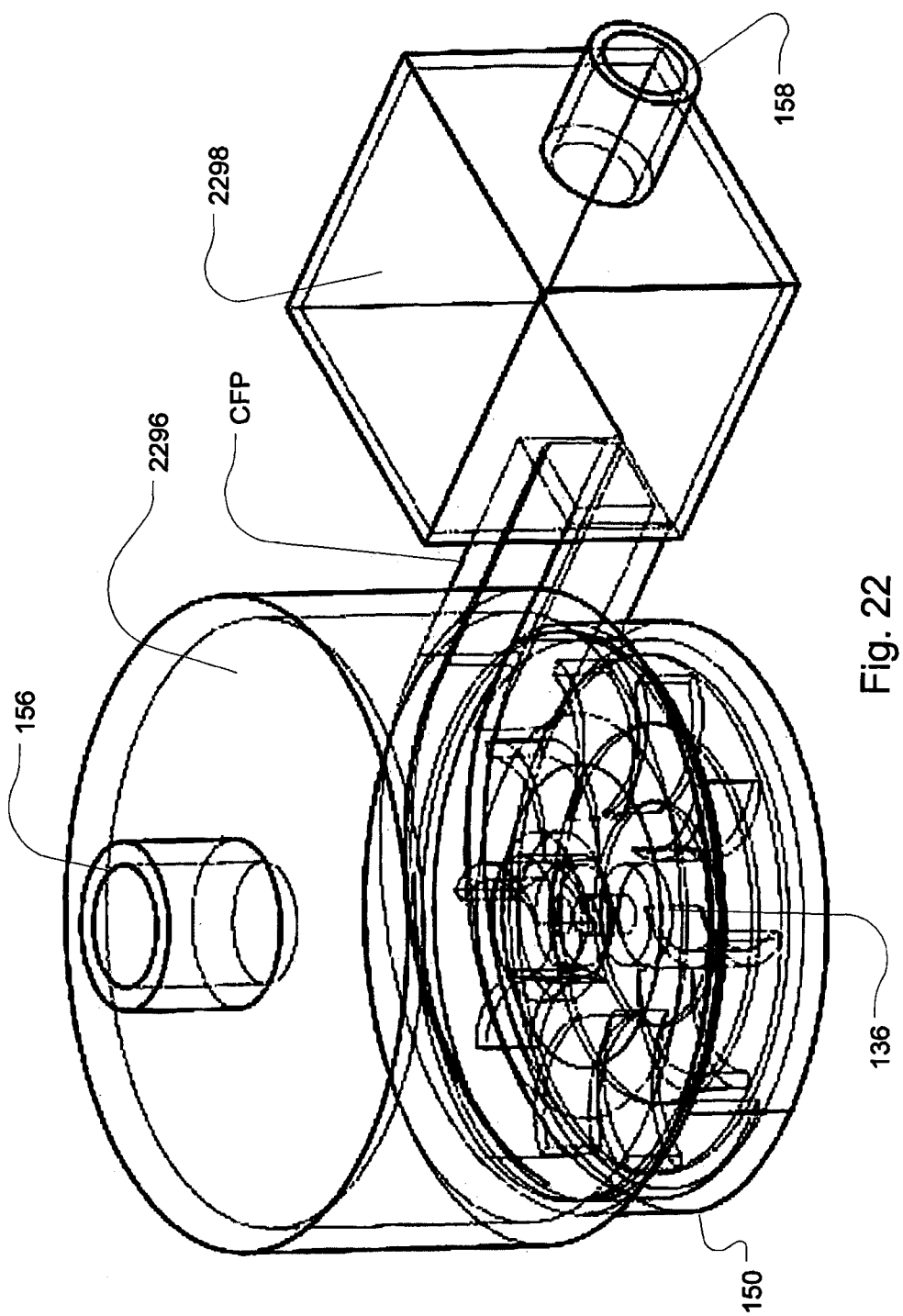
FIG. 22 is an isometric projection of an example embodiment of an airpath with an inlet muffler, blower volute, magnetic impeller and an outlet muffler.

In one example embodiment, the chamber with inlet and outlet paths may be implemented as a disposable unit. An example is illustrated in FIG. 22. As shown, inlet 156 may lead to an inlet muffler 2296, or other structure configured to reduce noise, in a muffler area leading to the blower partition. The chamber 150 may include features of the other embodiments described in this specification, such as the blower partition with any of the volute assemblies or volute inserts previously described. The disposable chamber may then include the impeller 136 such as the magnetic impeller. The chamber 150 may also be coupled to an outlet muffler 2298 in a discrete container but connected to the impeller's flow by a connective flow path CFP. The outlet muffler 2298, or other structure configured to reduce noise, may lead to the outlet 158 on the outlet muffler container. In operation, the disposable unit may be placed on a base as previously described and may be refilled with water for use as desired. The unit's components may have a particular life span, such as the wear life of the impeller or chamber, and may be replaced when their useful life has expired. In such a case, a new replacement chamber unit may then be used with the original base.

Figure 23:
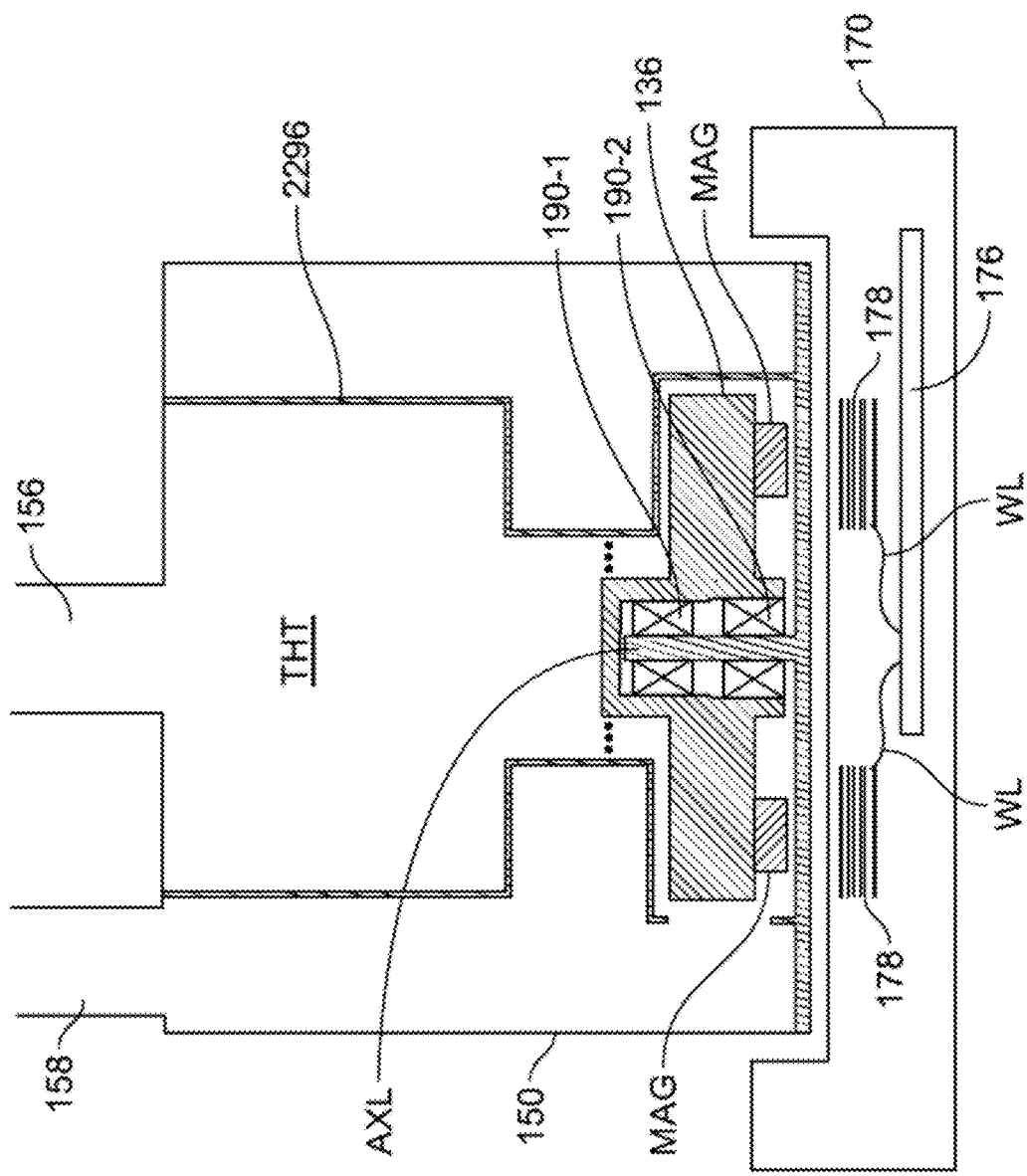
FIGS. 23 and 24 show examples of a chamber with concentric inlet and outlet flow paths including an inlet muffler.

In the embodiment of FIG. 23, which may also be implemented as a disposable unit, concentric inlet and outlet flow paths of the chamber, similar to other embodiments, may be configured to include the inlet muffler. In such a case, the throat THT of the inlet muffler may be surrounded by a portion of the outlet path. In the example, a discrete outlet muffler container like that of FIG. 22 need not be implemented because a common container houses the inlet muffler and the outlet flow path, such as in the illustrated concentric fashion. In this embodiment, the coils are in the base 170 but are coupled to the PCB 176 with wire leads WL rather than being integrated on the PCB 176 itself.

Figure 24:
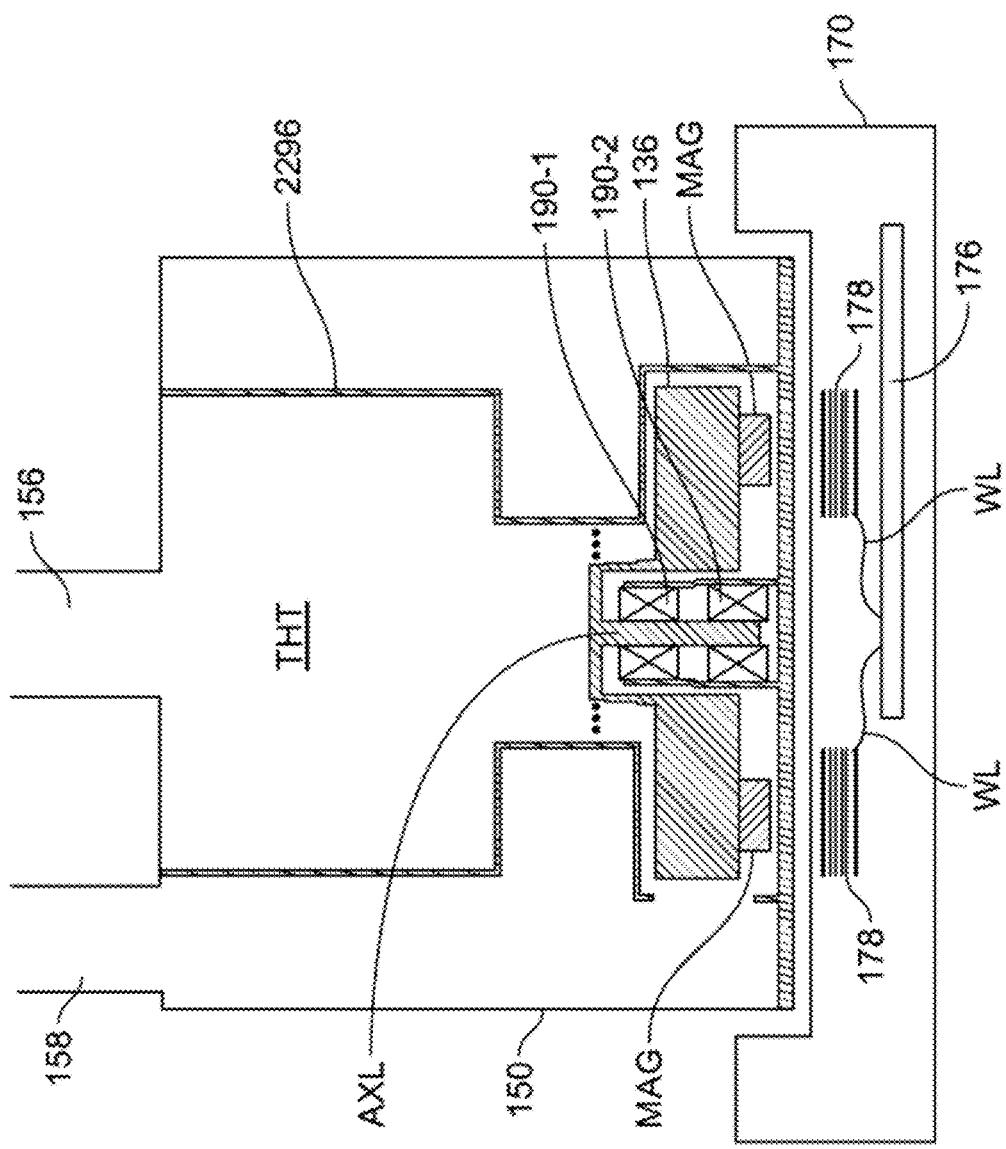

In the illustrated embodiment of FIG. 23, the impeller rotates on an axle that may optionally be an integrated component of the inlet muffler insert, the chamber bottom or a bottom plate. The impeller 136 with magnets MAG (or an otherwise magnetized impeller) and an impeller shaft may rotate about the axle on one or more bearings 190-1, 190-2, such as two contact rolling element bearings as illustrated in FIG. 23. Such additional bearings may help to promote stability and/or alignment in the rotation of the impeller and may thereby reduce noise, and/or increase life, of the respiratory apparatus in operation. In a disposable embodiment, one bearing with reduced tolerance in rotor alignment might be implemented and may permit a reduction in cost suitable for a shorter required lifespan of such an apparatus. A similar example that may be implemented as a disposable unit is shown in FIG. 24. However, in FIG. 24, the inlet muffler insert, the chamber bottom or a bottom plate may have a stationary sleeve to locate the bearings, and a shaft of the impeller rotates within the sleeve.

Figure 25:
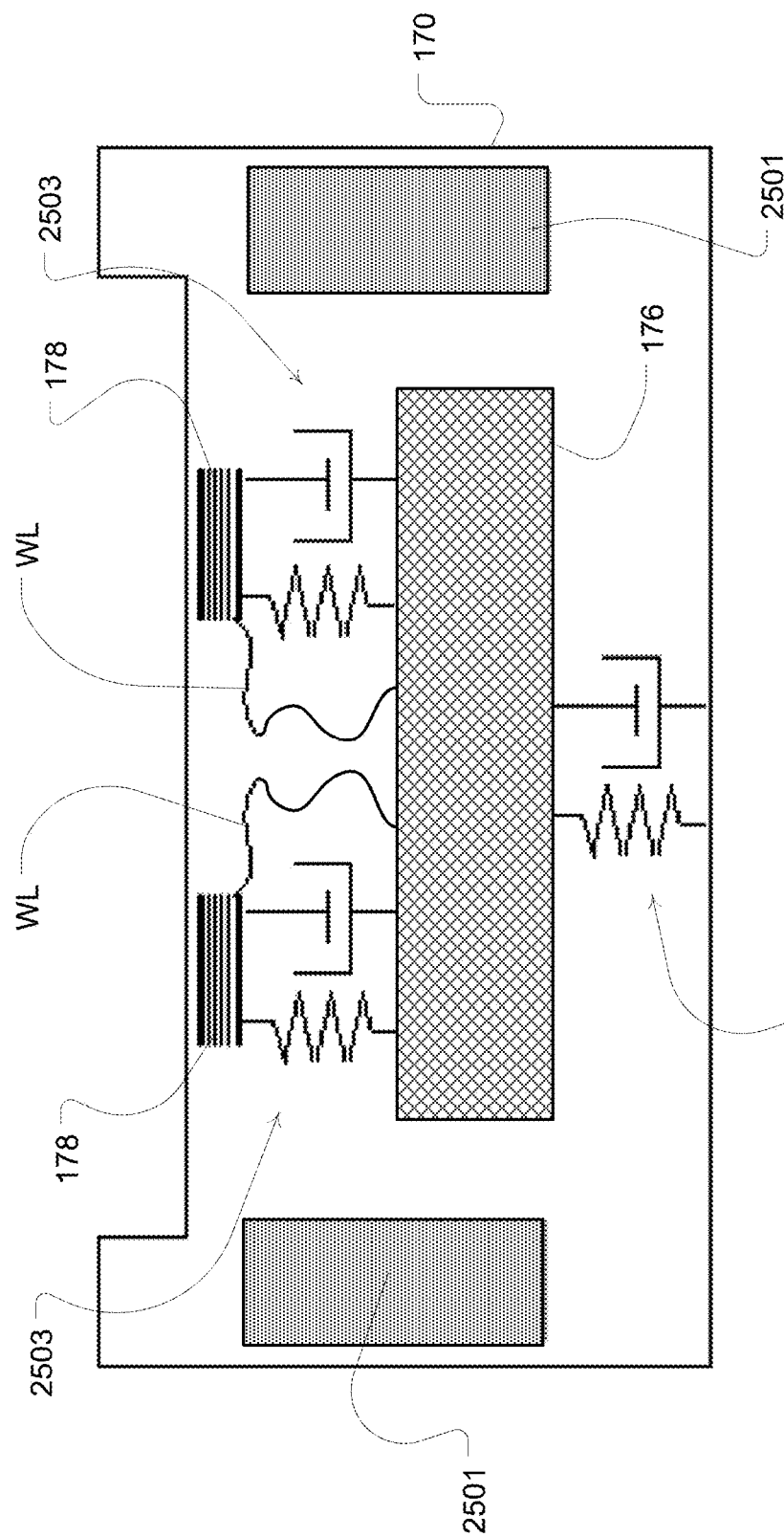
FIG. 25 illustrates a base including components that may be suitable to reduce coil vibration or noise of operation.

In FIG. 25, a base is illustrated with optional components that may assist in noise reduction such as by reducing coil vibration. Alternatively, a vibration isolation system may increase the vibration in the coils in the audible frequency range, channelling the fluctuating energy in the motor or blower system into the coils in the form of oscillation between kinetic energy in their mass and deformation in their suspension system. Optionally, since the coils may oscillate at higher frequencies and potentially create noise, the base may include acoustic damping materials or sound insulation 2501 within the base to encase such sound and thereby prevent it from traveling out of the base or to the patient accessible flow paths. In some examples, the coils 178 and the PCB 176 control circuit (processors) may include one or more vibration absorbers 2503. In some embodiments, each may have one or more discrete vibration absorbers. For example, a spring and/or damping mechanism may be configured to reduce vibrations of each component. In some versions, the coils may be made to be lighter than the magnets of the impeller and/or the coils may be mounted with softer springs. At higher frequencies, the equal and opposite forces acting between the magnets and coils would then permit a greater displacement in the coils compared to that in the magnets, which may thereby reduce the magnets' vibrations. Since the resulting coil vibration may be more readily contained in the base with acoustic isolation materials compared to the vibrations that occur in any flow path that is accessible to the patient, such a configuration may reduce noise. In fact, the isolation of the coils away from the flow path and into the base as previously described may permit noise reductions compared to other blowers that include the control coils and magnets in the flow path.

Wear Sensor

Some embodiments may include a wear sensor to monitor operational condition of the impeller components. For example, an accelerometer may be implemented to generate a measure of vibration of the impeller during operation, such as when the impeller is set to a predetermined state, such as a predetermined speed or set to deliver a predetermined pressure. A controller of the respiratory apparatus may periodically control the sensing of the measure of vibration at the predetermined state. An increase in the vibration measure from a previously specified, standard or tested measure or an increase of a certain amount above the prior measure, may be taken as an indication of increased impeller vibration and/or that the impeller may need to be replaced. In such a case, the controller of the apparatus or a processor thereof may compare the current measure to the previous standard measure or some other threshold and control a generation of a warning message or indication light for replacement of the impeller component based on the threshold comparison. In some embodiments, a microphone may serve as the vibration/noise sensor and the vibration measure may be a measure of noise from the microphone.

Multiple Respiratory Apparatuses

In certain embodiments two or more respiratory apparatuses 112, 212 may be coupled together to provide higher levels of pressure support, for example for Bilevel therapy where a higher inspiratory positive airway pressure IPAP is provided during inspiration and a lower expiratory positive airway pressure EPAP is provided during expiration. The respiratory apparatus 112, 212 may be coupled together via a valve that allows for pressure generated from both respiratory apparatuses to be provided to the patient during IPAP whilst pressure from only one respiratory apparatus is provided to the patient during EPAP.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from respiratory disorders and/or OSA, it is to be appreciated that patients who suffer from other illnesses (e.g., diabetes, morbid obesity, stroke, bariatric surgery, etc.) can derive benefit from the above teachings. Moreover, the above teachings' have applicability with patients and non-patients alike in non-medical applications.

What is claimed is:

1. A respiratory apparatus for delivery of a pressurized breathable gas to a patient's airways for respiratory treatment, the respiratory apparatus comprising:

a chamber including an air inlet and an air outlet;

a base configured to receive the chamber thereon; and a motor configured to provide a supply of pressurized air to the air outlet, the motor having (a) a stationary portion comprising a stator having a plurality of wound coils, and (b) a rotating portion comprising an impeller having a plurality of rotor magnets;

wherein the stationary portion of the motor is located in the base and the rotating portion of the motor is located in the chamber, wherein the chamber separates the rotating portion from the base, wherein the plurality of rotor magnets and the stator are configured in a stacked arrangement such that the plurality of rotor magnets are positioned over the plurality of wound coils in use, and wherein the air outlet is adapted to be coupled to a patient conduit for delivery of the pressurized breathable gas to the patient's airways.

2. The respiratory apparatus of claim 1, wherein, in use, the impeller is magnetically driven to rotate by the stationary portion in the base.

3. The respiratory apparatus of claim 2, wherein the impeller is constructed of a magnetized polymer.

4. The respiratory apparatus of claim 2, wherein the rotating portion forms part of a blower within the chamber.

5. The respiratory apparatus of claim 4, wherein the blower comprises an inlet flow path configured to direct air from the air inlet to the impeller.

6. The respiratory apparatus of claim 4, wherein the blower comprises a volute configured to direct the supply of pressurized air from the impeller towards one or more blower outlets.

7. The respiratory apparatus of claim 1, wherein the stationary portion includes the stator having a plurality of wound coils aligned horizontally in the base.

8. The respiratory apparatus of claim 1, wherein the chamber is further configured to hold a supply of water to humidify the supply of pressurized air or gas prior to exiting through the air outlet.

9. The respiratory apparatus of claim 8, wherein the supply of water is heated by a heater element.

10. The respiratory apparatus of claim 9, wherein the heater element is located in the base.

11. The respiratory apparatus of claim 9, wherein the heater element is located in the chamber.

12. The respiratory apparatus of claim 1, wherein for operation, the stationary portion and the rotating portion are separated by a housing wall of the base.

13. The respiratory apparatus of claim 12, wherein the rotating portion and the stationary portion are further separated by a wall of the chamber.

14. The respiratory apparatus of claim 1, wherein the chamber has a container configuration including a bottom wall and side wall.

15. The respiratory apparatus of claim 1, wherein the chamber comprises a spiral flow pathway.

16. The respiratory apparatus of claim 15, wherein a blower partition is configured to expel pressurized air at a bottom wall of the chamber and into the spiral flow pathway and the spiral flow pathway is configured to deliver the pressurized air to the air outlet proximate the top of the chamber.

17. The respiratory apparatus of claim 1, wherein an inlet pathway comprises a muffler.

18. The respiratory apparatus of claim 1, wherein an outlet pathway of the respiratory apparatus comprises a muffler.

19. The respiratory apparatus of claim 1, wherein the plurality of wound coils are field coils for influencing the operation of the rotating portion, and wherein each field coil includes a vibration absorber.

20. The respiratory apparatus of claim 1, wherein the rotating portion of the motor and the stationary portion of the motor are configured in the stacked arrangement to create a direction of magnetic flux between the rotor magnets and the stator for operation, wherein the direction of the magnetic flux is parallel to an axis of rotation of the impeller.

* * * * *